(12) United States Patent
Kovacs et al.

(10) Patent No.: US 10,294,454 B2
(45) Date of Patent: May 21, 2019

(54) METHODS AND KITS FOR CELL ACTIVATION

(71) Applicant: General Electric Company, Schenectady, NY (US)

(72) Inventors: Ernest William Kovacs, Cohoes, NY (US); Anup Sood, Clifton Park, NY (US); Reginald Donovan Smith, Schenectady, NY (US); Evelina Roxana Loghin, Rexford, NY (US); Padmaparna Chadhuri, Bangalore (IN); Vandana Keskar, Niskayuna, NY (US); Chrystal Mae Chadwick, Latham, NY (US); Martin James Brown, Ballston Spa, NY (US)

(73) Assignee: General Electric Company, Schenectady, NY (US)

( * ) Notice: Subject to any disclaimer, the term of this patent is extended or adjusted under 35 U.S.C. 154(b) by 17 days.

(21) Appl. No.: 15/245,584

(22) Filed: Aug. 24, 2016

(65) Prior Publication Data

US 2018/0057791 A1 Mar. 1, 2018

(51) Int. Cl.
*A61K 38/00* (2006.01)
*C12N 5/00* (2006.01)
*C12N 5/02* (2006.01)
*C12N 5/0783* (2010.01)
*C07K 16/28* (2006.01)

(52) U.S. Cl.
CPC ........ *C12N 5/0636* (2013.01); *C07K 16/2809* (2013.01); *C07K 16/2818* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| | | | |
|---|---|---|---|
| 5,506,121 A | 4/1996 | Skerra et al. | |
| 5,635,602 A | 6/1997 | Cantor | |
| 5,658,741 A | 8/1997 | Bolton et al. | |
| 5,858,358 A | 1/1999 | June et al. | |
| 5,872,222 A | 2/1999 | Chang | |
| 6,077,833 A | 6/2000 | Bennett et al. | |
| 6,103,493 A | 8/2000 | Skerra et al. | |
| 6,106,835 A | 8/2000 | Chang | |
| 6,117,982 A | 9/2000 | Chang | |
| 6,129,916 A | 10/2000 | Chang | |
| 6,197,298 B1 | 3/2001 | Chang | |
| 6,248,564 B1 | 6/2001 | Walker et al. | |
| 6,268,411 B1 | 7/2001 | Schneck et al. | |
| 6,270,772 B1 | 8/2001 | Burrows et al. | |
| 6,448,071 B1 | 9/2002 | Schneck et al. | |
| 6,458,354 B1 | 10/2002 | Schneck et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,897,067 B2 | 5/2005 | Uhler | |
| 6,902,933 B2 | 6/2005 | Uhler | |
| 6,905,681 B1 | 6/2005 | June et al. | |
| 7,056,741 B2 | 6/2006 | Uhler | |
| 7,268,219 B1 | 9/2007 | Savage | |
| 7,541,184 B2 | 6/2009 | Berenson et al. | |
| 7,572,631 B2 | 8/2009 | Berenson et al. | |
| 7,592,431 B2 | 9/2009 | Har-Noy | |
| 7,927,595 B1 | 4/2011 | June et al. | |
| 7,973,137 B1 | 7/2011 | Schneck et al. | |
| 8,012,750 B2 | 9/2011 | Har-Noy | |
| 8,617,884 B2 | 12/2013 | Berenson et al. | |
| 8,637,307 B2 | 1/2014 | June et al. | |
| 9,862,908 B2 | 1/2018 | Chen et al. | |
| 2002/0051783 A1 | 5/2002 | Savage | |
| 2002/0058019 A1 | 5/2002 | Berenson et al. | |
| 2002/0091079 A1 | 7/2002 | Rhode et al. | |
| 2002/0115214 A1 | 8/2002 | June et al. | |
| 2002/0122818 A1 | 9/2002 | Albani | |
| 2002/0127231 A1 | 9/2002 | Schneck et al. | |
| 2002/0198144 A1 | 12/2002 | Wong et al. | |
| 2003/0044415 A1 | 3/2003 | Savage | |
| 2003/0072796 A1 | 4/2003 | Cai et al. | |
| 2003/0083474 A1 | 5/2003 | Schmidt | |
| 2003/0119185 A1 | 6/2003 | Berenson et al. | |
| 2003/0127382 A1 | 7/2003 | Miltenyi et al. | |
| 2003/0224520 A1 | 12/2003 | June et al. | |
| 2003/0229020 A1 | 12/2003 | Yuqiu et al. | |
| 2003/0235908 A1 | 12/2003 | Berenson et al. | |
| 2004/0001829 A1 | 1/2004 | June et al. | |
| 2004/0005298 A1 | 1/2004 | Bonyhadi et al. | |
| 2004/0028692 A1 | 2/2004 | Zitvogel | |
| 2004/0082012 A1 | 4/2004 | Busch et al. | |
| 2004/0091488 A1 | 5/2004 | Seeman et al. | |
| 2004/0096429 A1 | 5/2004 | Savage | |

(Continued)

FOREIGN PATENT DOCUMENTS

EP 0421380 B1 12/1995
EP 0 678 034 B1 5/1999

(Continued)

OTHER PUBLICATIONS

Ceuppens et al., "Monoclonal Antibodies to the CD5 Antigen can Provide the Necessary Second Signal for Activation of Isolated Resting T cells by Solid-Phase-Bound OKT3", The Journal of Immunology, vol. 137, Issue 6, pp. 1816-1821, Sep. 15, 1986.

(Continued)

*Primary Examiner* — Michail A Belyavskyi
(74) *Attorney, Agent, or Firm* — Eversheds Sutherland (US) LLP

(57) ABSTRACT

Provided are methods and kits for activating T cells, the method comprising providing a population of T cells, adding a plurality of first agents, where the first agent comprises a T-cell activator and a first binder moiety, and adding a second agent comprising a plurality of capture oligomers, where at least a segment of at least one of the plurality of capture oligomers is capable of associating with the first binder moiety. The method further comprises incubating the population of T cells, whereby at least a portion of the population of T cells is activated.

25 Claims, 20 Drawing Sheets

Specification includes a Sequence Listing.

(56) References Cited

U.S. PATENT DOCUMENTS

| | | |
|---|---|---|
| 2004/0115216 A1 | 6/2004 | Schneck et al. |
| 2004/0137617 A1 | 7/2004 | Luxembourg et al. |
| 2004/0151704 A1 | 8/2004 | Berenson et al. |
| 2004/0175373 A1 | 9/2004 | Berenson et al. |
| 2004/0203155 A1 | 10/2004 | June et al. |
| 2004/0209295 A1 | 10/2004 | Schwabe et al. |
| 2004/0224402 A1 | 11/2004 | Bonyhadi et al. |
| 2005/0084967 A1 | 4/2005 | Berenson et al. |
| 2005/0175583 A1 | 8/2005 | Tamarkin et al. |
| 2005/0191291 A1 | 9/2005 | Har-Noy |
| 2005/0214274 A1 | 9/2005 | Har-Noy |
| 2006/0013832 A1 | 1/2006 | June et al. |
| 2006/0140919 A1 | 6/2006 | June et al. |
| 2006/0205069 A1 | 9/2006 | June et al. |
| 2006/0246587 A1 | 11/2006 | June et al. |
| 2007/0036783 A1 | 2/2007 | Humeau et al. |
| 2007/0172490 A1 | 7/2007 | Scholz |
| 2008/0038282 A1 | 2/2008 | Napper et al. |
| 2008/0207485 A1 | 8/2008 | Schwabe |
| 2008/0279836 A1 | 11/2008 | Har-Noy |
| 2009/0017000 A1 | 1/2009 | Cai et al. |
| 2009/0155836 A1 | 6/2009 | June et al. |
| 2010/0068193 A1 | 3/2010 | Brunsvig et al. |
| 2010/0143905 A1 | 6/2010 | Lane et al. |
| 2010/0226854 A1 | 9/2010 | Schoeller et al. |
| 2010/0284965 A1 | 11/2010 | Fahmy et al. |
| 2011/0014217 A1 | 1/2011 | Fahmy et al. |
| 2011/0318380 A1 | 12/2011 | Brix et al. |
| 2012/0045767 A1 | 2/2012 | Lau et al. |
| 2013/0052733 A1 | 2/2013 | Chang |
| 2013/0171668 A1 | 7/2013 | Loeset et al. |
| 2013/0289253 A1 | 10/2013 | Luescher et al. |
| 2014/0087462 A1 | 3/2014 | Scheffold et al. |
| 2014/0295458 A1 | 10/2014 | Schmidt et al. |
| 2014/0349315 A1 | 11/2014 | Loeset et al. |
| 2014/0370099 A1 | 12/2014 | Green et al. |
| 2015/0024411 A1 | 1/2015 | Stadler |
| 2015/0166997 A1 | 6/2015 | Messmer |
| 2015/0366991 A1 | 12/2015 | Schneck et al. |
| 2016/0017058 A1 | 1/2016 | Kim et al. |
| 2016/0024470 A1 | 1/2016 | Aarvak et al. |
| 2016/0051698 A1 | 2/2016 | Schneck et al. |
| 2016/0068811 A1 | 3/2016 | Kokaji |
| 2016/0129133 A1 | 5/2016 | McCreedy |

FOREIGN PATENT DOCUMENTS

| | | |
|---|---|---|
| EP | 1 497 428 A2 | 1/2005 |
| EP | 0 824 594 B1 | 4/2005 |
| EP | 1 526 171 A1 | 4/2005 |
| EP | 1 330 516 B1 | 1/2007 |
| EP | 1 093 465 B1 | 9/2007 |
| EP | 1 989 292 A2 | 11/2008 |
| EP | 1 123 086 B1 | 3/2010 |
| EP | 1 594 958 B1 | 10/2010 |
| EP | 1 586 655 B1 | 7/2012 |
| EP | 1 434 856 B1 | 7/2013 |
| EP | 2 034 009 B1 | 1/2014 |
| WO | 1994012196 A1 | 6/1994 |
| WO | 1994/015635 A1 | 7/1994 |
| WO | 1994029436 A1 | 12/1994 |
| WO | 1995033823 A1 | 12/1995 |
| WO | 1998010284 A1 | 3/1998 |
| WO | 2002/042447 A2 | 5/2002 |
| WO | 2003/024989 A2 | 3/2003 |
| WO | 2003/067221 A2 | 8/2003 |
| WO | 2003/089600 A2 | 10/2003 |
| WO | 2004/065590 A2 | 8/2004 |
| WO | 20050049085 A1 | 6/2005 |
| WO | 2007/110785 A2 | 10/2007 |
| WO | 2012/024695 A1 | 2/2012 |
| WO | 20140076277 A1 | 5/2014 |
| WO | 20150158868 A3 | 1/2016 |

OTHER PUBLICATIONS

Baroja et al., "The Anti-T cell Monoclonal Antibody 9.3 (anti-CD28) Provides a Helper Signal and Bypasses the Need for Accessory Cells in T cell Activation with Immobilized Anti-CD3 and Mitogens", Cellular Immunology, vol. 120, Issue 1, pp. 205-217, Apr. 1989.

Riddell et al., "The Use of Anti-CD3 and Anti-CD28 Monoclonal Antibodies to Clone and Expand Human Antigen-Specific T cells", Journal of Immunological Methods, vol. 128, Issue 2, pp. 189-201, Apr. 17, 1990.

Norman, "Mechanisms of Action and Overview of OKT3", Therapeutic Drug Monitoring, vol. 17, Issue 6, pp. 615-620, Dec. 1995.

Rush et al., "Efficient Priming of CD4 and CD8 T Cells by DNA Vaccination Depends on Appropriate Targeting of Sufficient Levels of Immunologically Relevant Antigen to Appropriate Processing Pathways", The Journal of Immunology, vol. 169, pp. 4951-4960, 2002.

Minquet et al., "Full Activation of the T cell Receptor Requires both Clustering and Conformational Changes at CD3", Immunity, vol. 26, Issue 1, pp. 43-54, Jan. 2007.

Dollins et al., "Assembling OX40 Aptamers on a Molecular Scaffold to Create a Receptor-Activating Aptamer", Chemistry & Biology, vol. 15, Issue 7, pp. 675-682, Jul. 21, 2008.

Dave, "Hierarchical Role of CD3 Chains in Thymocyte Development", Immunol. Rev. 232, pp. 22-33, 2009.

"IBA Announces its Partnership with Beckman Coulter for the Distribution of IBA's Streptamer Product Portfolio", Bionity, http://www.bionity.com/en/news/117192/iba-announces-its-partnership-with-beckman-coulter-for-the-distribution-of-iba-s-streptamer-product-portfolio.html, May 5, 2010.

Gangar et al., "Programmable Self-Assembly of Antibody-Oligonucleotide Conjugates as Small Molecule and Protein Carriers", Journal of American Chemical Society, vol. 134, Issue 6, pp. 2895-2897, Feb. 2012.

Abbas et al., "Activation of T lymphocytes", Immunology, Chapter 9, http://www.slideshare.net/princesa_mera/immunology-chapter-9-activation-of-t-lymphocytes, Dec. 8, 2012.

Matic et al., "Fine Tuning and Efficient T Cell Activation with Stimulatory a CD3 Nanoarrays", Nano Letters, American Chemical Society, vol. 13, pp. 5090-5097, 2013.

Essand et al., "Genetically Engineered T cells for the Treatment of Cancer", Journal of Internal Medicine, vol. 273, Issue 2, pp. 166-181, Feb. 2013.

Abendroth, F., et al., "DNA-controlled bivalent presentation of ligands for the estrogen receptor," Angewandte Chemie International Edition, vol. 50, pp. 8592-8596 (2011).

"Adaptimmune gains licensing rights to Life Tech antibody-coated magnetic beads," Retrieved from the Internet URL: https://www.pctcelltherapy.com/industry-news/2013/01/10/adaptimmune-gains-licensing-rights-to-life-tech-antibody-coated-magnetic-beads, on Aug. 9, 2018, pp. 1-2, (Jan. 8, 2013).

Ali, M.M. et al., "Rolling circle amplification: a versatile tool for chemical biology, materials science and medicine," Chemical Society Reviews, vol. 43, No. 10, pp. 3324-3341, (May 2014).

Dako Products, "Retrieved from the Internet URL: http://www.dako.com/08065_15dec05_guide_to_flow_cytometry_mhc_multimers_chapter12.pdf, on Jul. 31, 2018, pp. 1-3 (Jul. 2018)".

Fauser, A.A., "Long-term expression of gene introduction into normal human T-lymphocytes by retroviral-mediated gene transfer," Journal of Cellular Biochemistry, vol. 45, Issue 4, pp. 353-358, (1991) (Abstract).

Kim, C. H., et al., "Synthesis of Bispecific Antibodies using Genetically Encoded Unnatural Amino Acids," Journal of the American Chemical Society, vol. 134, pp. 9918-9921 (2012).

Ledbetter, J. A., et al., "CD28 Ligation in T-cell Activation: Evidence for Two Signal Transduction Pathways," Blood, vol. 75, No. 7, pp. 1531-1539 (Apr. 1990).

Poltorak, M., et al., "TCR activation kinetics and feedback regulation in primary human T cells," Cell Communication and Signaling, Retrieved from the Internet URL: http://www.biosignaling.com/content/pdf/1478-811X-11-4.pdf, on Jul. 31, 2017 pp. 1-11 (2013).

(56) References Cited

OTHER PUBLICATIONS

Sharpe, M., and Mount, N., " Genetically modified T cells in cancer therapy: opportunities and challenges," Disease Models & Mechanisms, Retrieved from the Internet URL: http://dmm.biologists.org/content/dmm/8/4/337.fµLI.pdf, on Jul. 31, 2018, pp. 337-350 (2015).

Taylor, L. P., et al., "Phenobarbital rheumatism in patients with brain tumor," Annals of Neurology, vol. 25, No. 1, pp. 92-94 (Jan. 1989).

Zhang, Z., et al., "DNA-scaffolded multivalent ligands to modulate cell function," Chembiochem, vol. 15, No. 9, pp. 1268-1273, (2014).

"Life Technologies Enters into an Exclusive License and Supply Agreement for Dynabeads," Life Technologies Corporation, Retrieved from the Internet URL:https://www.pmewswire.com/news-releases/life-technologies-enters-into-an-exclusive-license-and-supply-agreement-for-dynabeads-217738051.html, on Aug. 9, 2018, pp. 1-4, (Jul. 31, 2013).

International Search Report and Written Opinion issued in connection with corresponding PCT Application No. PCT/US2017/048306 dated Nov. 16, 2017.

METHODS AND KITS FOR CELL ACTIVATION

SEQUENCE LISTING

The instant application contains a Sequence Listing which has been submitted electronically in ASCII format and is hereby incorporated by reference in its entirety. Said ASCII copy, created on Sep. 26, 2016, is named 312704-1_SL.txt and is 2,065 bytes in size.

BACKGROUND

Cellular therapies, T cell therapies in particular, have shown remarkable success in treating hematological tumors and show promise in the treatment of solid tumors. These treatments require isolation of a patient's PBMC's or T cells and subsequent expansion (activation and proliferation) to generate a personalized therapeutic dose.

For the most part this type of personalized therapy consists of removing blood cells from cancer patients; isolating and activating T cells; genetically modifying the T cells thereby programming those cells to recognize and attack cancer cells; expanding the T cells; and, lastly, introducing those cells back into the body so the patient's immune system can take over. Activation is a critical component of the whole process as it is required for efficient introduction of genetic material and for robust expansion.

Several technology platforms exist in the commercial space, super paramagnetic, nonpyrogenic polystyrene beads with antibodies covalently bound to the surface, such as Dynabeads® CD3/CD28 CTS™ (Life Technologies, Beverly, Mass.) is one of the most widely used to provide for isolation, activation and expansion of T cells. Still, in using bead based clustering and cell activation, significant cell loss is observed using the bead platform. This is related to bead removal after cell expansion is complete. Alternate technologies, such as the activator from StemCell Technologies that circumvent the issue of bead removal, are not very effective for cell activation, particularly early in the activation phase when the viral transduction is generally carried out.

As such a new technology platform is desired that will provide novel approaches to cluster the T-cell surface receptors required for T cell activation and provide co-stimulatory signals to increase proliferation.

BRIEF DESCRIPTION

Disclosed herein are methods for activating T cells, the method comprising providing a population of T cells, adding a plurality of first agents, wherein the first agent comprises a T-cell activator and a first binder moiety; adding a second agent comprising a plurality of capture oligomers, wherein at least a segment of at least one of the plurality of capture oligomers is capable of associating with the first binder moiety; and incubating the population of T cells after steps (b) and (c), whereby at least a portion of the population of T cells is activated. The method may further comprise the addition of a T-cell co-stimulator.

In some embodiments, the present invention is a method for activating T cells, the method comprising providing a population of T cells, adding a plurality of first agents, wherein the first agent comprises a T-cell activator attached to a nucleic acid sequence; adding a nucleic acid polymer comprising a plurality of capture oligonucleotides, wherein at least a segment of at least one of the plurality of capture oligonucleotides is capable of associating with the nucleic acid sequence; and incubating the population of T cells after steps (b) and (c), whereby at least a portion of the population of T cells is activated. The method may further comprise the addition of a T-cell co-stimulator. In some embodiments the T-cell co-stimulator is attached to a nucleic acid sequence, wherein at least a segment of at least one of the plurality of capture oligonucleotides is capable of associating with the nucleic acid sequence attached to the T-cell co-stimulator.

In some embodiments the present invention relates to a kit comprising a T cell activator attached to a nucleic acid sequence; and a nucleic acid polymer comprising a plurality of capture oligonucleotide sequences, wherein the nucleic acid sequence is complementary to at least a segment of at least one of the capture oligonucleotide sequences.

DESCRIPTION OF THE FIGURES

FIG. 9A is a graphical representation of the same cultures in FIG. 9A showing x-fold cell expansion after days 4 and 7.

DETAILED DESCRIPTION

Figures 1A, 1B:
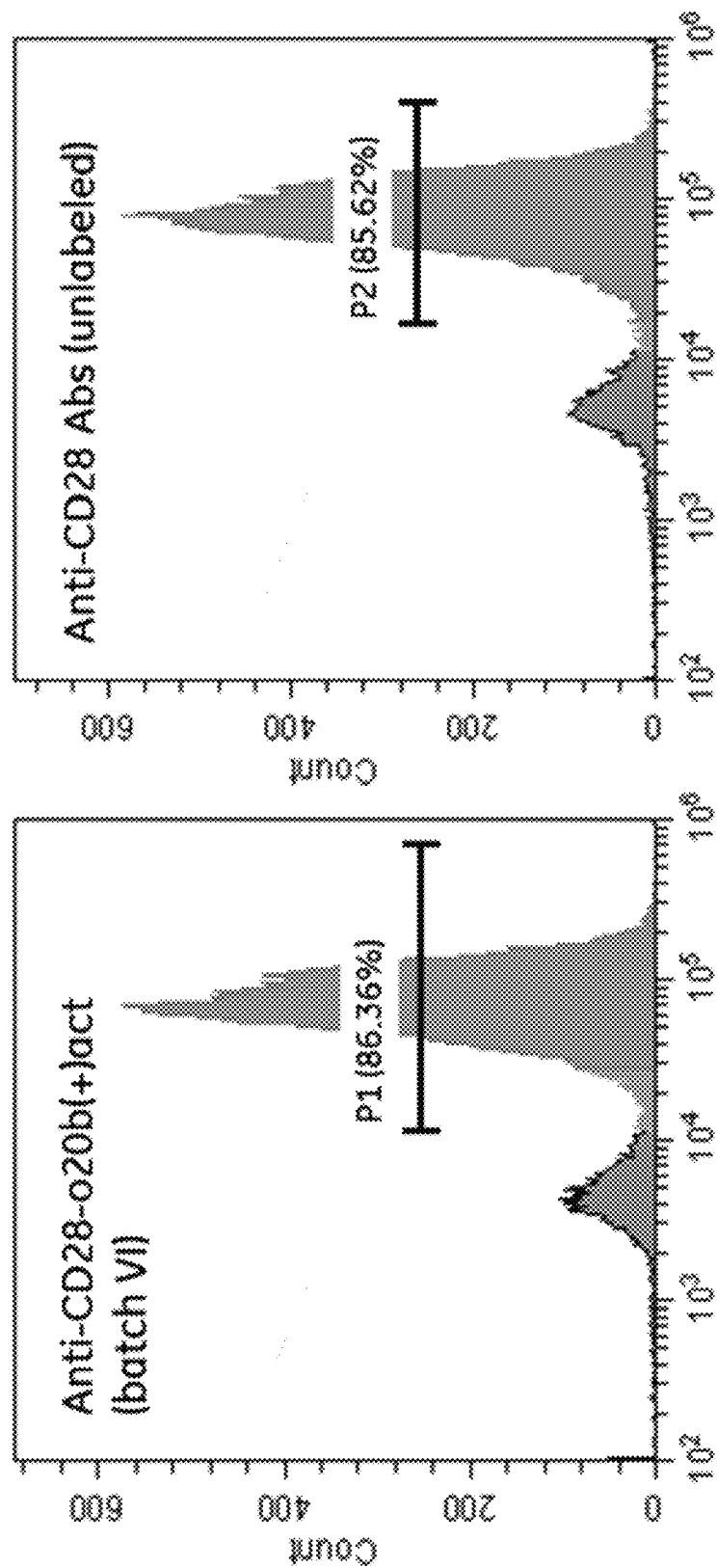
FIG. 1A-1E are representative flow cytometry histograms for positively validated anti-CD3-o20b(+)act and anti-CD28-o20b(+)act conjugates binding to T cells. 1A: Binding of a DNA (o20b(+)act) attached anti-CD28 antibody to T cells, 1B: Binding of corresponding unconjugated anti-CD28 antibody (positive control), 1C: Binding of a DNA (o20b(+)act) attached anti-CD3 antibody to T cells, 1D: Binding of corresponding unconjugated anti-CD3 antibody (positive control), and 1E, Cell incubated with labeled secondary antibody (negative control).
Figure 1C:
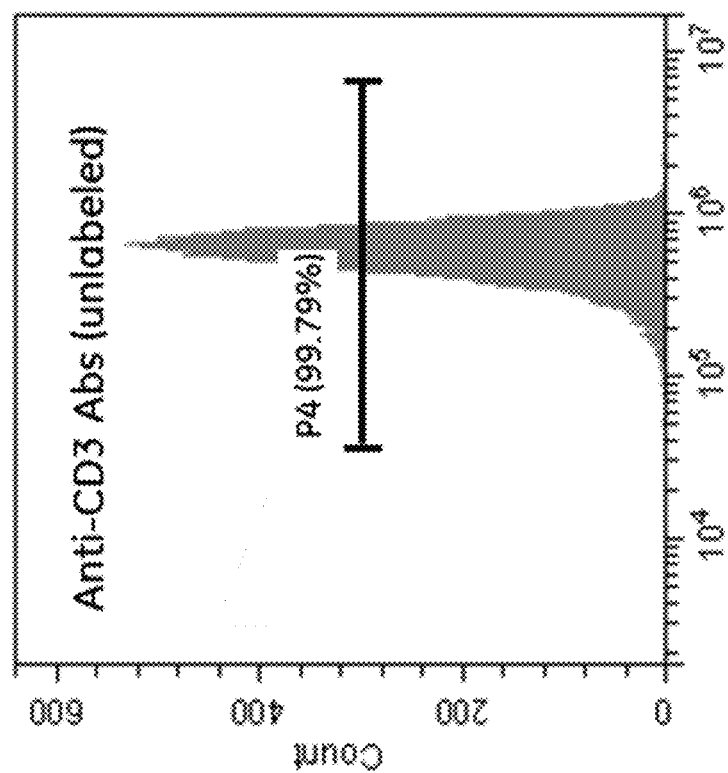
Figure 1D:
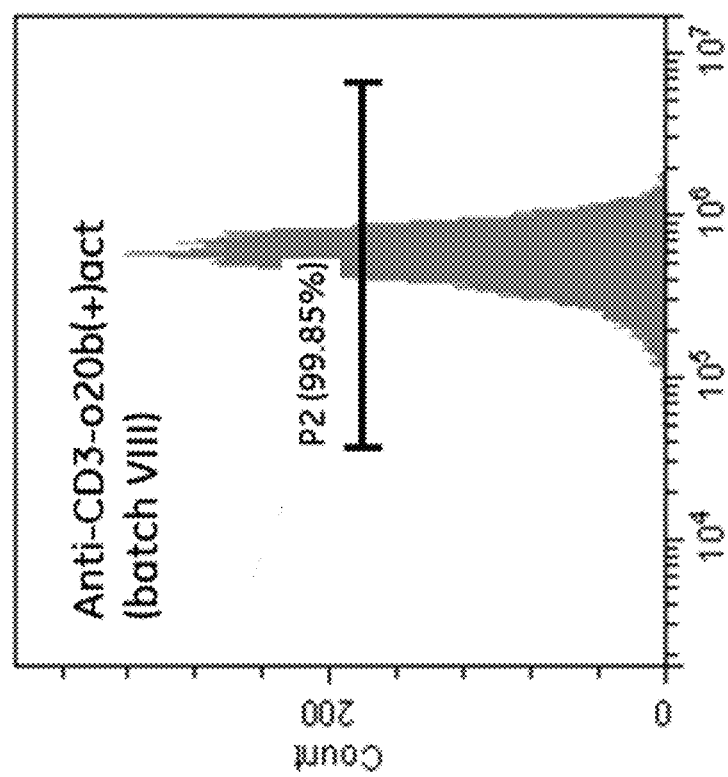
Figure 1E:
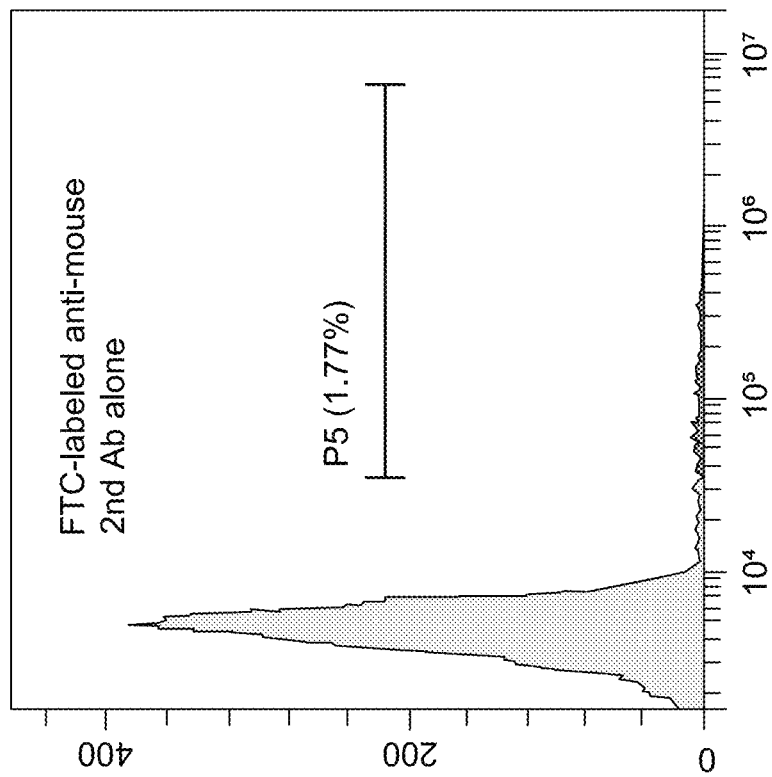

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

While certain embodiments are directed towards autologous cell therapies that involve collection, manipulation, and re-insertion of a patient's own cells, the applications of the disclosed techniques may include allogenic cells, modified human cells, or xenotransplantation of non-human cells. Cell based therapies that are contemplated as being used in conjunction with the disclosed techniques may include therapies for organ or tissue regeneration, cancer treatment, blood disorders, immunotherapies, heart disease, or any other cell-based therapies. A variety of cell types may be utilized within the context of the present invention including for example, but not limited to, cell types such as B cells, T-cells, or natural killer cells. The cells can be isolated from any tissue such as peripheral blood, bone marrow, or tumor tissue. Some embodiments are directed towards T cells enriched from peripheral blood by centrifugation using for example Ficoll-Paque™ or Percoll™ (GE Healthcare) gradient. Some other embodiments are directed towards a specific subpopulation of T-cells, such as CD28+, CD4+, CD8+, CD45RA+, and/or CD45RO+ T cells, further isolated by positive or negative selection techniques.

As used herein "second agent" refers to a polymer comprising a plurality of capture oligomers, wherein at least a segment of at least one of the plurality of capture oligomers is capable of associating with a first binder moiety. In some embodiments the second agent is a nucleic acid polymer such as a rolling circle amplification product and the "capture oligomer" is a capture oligonucleotide sequence. The nucleic acid polymer may comprise a plurality of the same or different capture oligonucleotide sequences. In some embodiments the number of capture oligonucleotide sequences in the nucleic acid polymer is greater than 3, preferably greater than 30, and more preferably greater than 300. In certain embodiments, the number of capture oligonucleotide sequences is greater than 2000. As such, the nucleic acid polymer may comprise a plurality of capture oligonucleotide sequences of the same or different nucleotide sequence, molecular weights, geometrical arrangements, and/or patterns of repetition. In some embodiments, the capture oligonucleotide sequence may have a length in range of from about 6 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, or from about 250 nucleotides to about 500 nucleotides. In some agents the second agent is double-stranded nucleic acid polymer while in other embodiments it is a single-stranded nucleic acid polymer. The nucleic acid polymer may include natural or unnatural nucleotides with modifications on the nucleic acid base, sugar or phosphate backbone. The second agent may further comprise spacer oligonucleotide sequences having different number and/or sequence of nucleotides than the capture oligonucleotide sequences, or non-nucleic acid spacer molecules. In some other embodiments the second agent is a cationic polymer comprising a plurality of capture cationic oligomers, containing contiguous stretches of cationic monomers such as histidine or lysine. The second agent may further comprise neutral or anionic spacer residues provided the overall charge remains cationic. In still other embodiments the second agent is an anionic polymer comprising a plurality of capture anionic oligomers, containing contiguous stretches of anionic monomers such as acrylate. The second agent may further comprise neutral or cationic spacer residues provided the overall charge is anionic.

As used herein, the term "first agent" refers to a cell activator attached to a "first binder moiety". In some embodiments, the cell activator is a T-cell activator. The term "first binder moiety" refers to a molecule that can associate with one or more capture oligomers. In some embodiments the first binder moiety is a nucleic acid sequence and the "second agent" is a nucleic acid polymer comprising a plurality of capture oligonucleotide sequences, such that the nucleic acid sequence of the first binder moiety is complementary to at least a segment of at least one of the plurality of capture oligonucleotide sequences. The nucleic acid sequence of the first binder moiety and the capture oligonucleotide sequence are capable of associating via complementary base-pair hybridization. The first binder moiety and the capture oligonucleotide may hybridize to form a double or triple helix structure depending on whether the nucleic acid polymer is a double-stranded nucleic acid polymer or a single-stranded nucleic acid polymer. In some embodiments, all the nucleotide residues of at least one capture oligonucleotide sequence may hybridize to complementary nucleotides in the first binder moiety. For example, at least one capture oligonucleotide sequence may have 50 nucleotide residues and all the 50 nucleotide residues may hybridize to complementary nucleotides in the first binder moiety. In some embodiments, all the nucleotides of the capture oligonucleotide sequence may not have corresponding complementary nucleotides in the nucleic acid sequence of the first binder moiety. In some embodiments, there may be one or more base-pair mismatches between the capture oligonucleotide sequence and the nucleic acid sequence of the first binder moiety. In still other embodiments the capture oligonucleotide sequence and/or the nucleic acid sequence of the first binder moiety may include nucleic acid analogs, with modified bases such as azidothymidine, inosine, or uridine, or modified sugars, e.g. 3'-OMe, or modified backbone, e.g. phosphorothioate, alkylphosphonate, phosphoramidate backbones. The first or second agent may further comprise non-complementary spacer oligonucleotide sequences or non-nucleic acid spacer molecules. In some other embodiments the first binder moiety is an anionic moiety such as a nucleic acid sequence, alginate, polyglutamate, polyaspartate or hyaluronate and the second agent is a polymer comprising a plurality of cationic capture oligomers. The anionic first binder moiety is capable of associating with at least a segment of at least one of the plurality of cationic capture oligomers via electrostatic association. In still other embodiments, the first binder moiety is a cationic moiety and the second agent is a polymer comprising a plurality of anionic capture oligomers.

As used herein, the term "T-cell activator" refers any agent that can activate a T-cell for proliferation and/or transduction. Suitable examples of T-cell activator include small organic molecules (for example ionomycin, phorbol myristate or acetate), natural or modified peptides, proteins (for example antibodies or affibodies), non-natural peptide mimics, nucleic acids (for example polynucleotides, PNA, DNA, RNA or aptamers), polysaccharides (for example lectins or sugars), lipids, enzymes, enzyme substrates or inhibitors, ligands, receptors, antigens, or haptens. In some embodiments, the T-cell activator binds to a T-cell surface receptor, such as a T-cell activating receptor, which results in delivery of a primary activation signal in a T-cell. T-cell activating receptors include for example T-Cell Receptor (TCR) or CD3 receptor. A primary activation signal can be initiated through binding between a TCR and an antigen presented in conjunction with either MHC class I or class II molecules, in order to stimulate an antigen-specific T-cell activation. A primary activation signal can also be initiated through binding between a CD3 receptor and a ligand targeted to the CD3 receptor, in order to stimulate a polyclonal T-cell activation. In exemplary embodiments the T-cell activator is an anti-CD3 antibody or fragments thereof. Other examples of T-cell activator include concanavalin A, protein kinase C (PKC) activator such as a phorbol ester (for example phorbol myristate acetate) or calcium ionophore (for example ionomycin which raises cytoplasmic calcium concentrations) and others. In some embodiments a first agent that binds to a TCR or a CD3 receptor may be used in conjunction with other T-cell activators.

In some embodiments, the method of activating T cells comprises the addition of a plurality of a $1^{st}$ population of first agents, wherein all the first agents in the $1^{st}$ population of first agents comprises T-cell activator of the same type, such as an anti-CD3 antibody. In some embodiments, the method may further comprise the addition of a $2^{nd}$, $3^{rd}$, ... $n^{th}$ population of first agents. The T-cell activators among different populations of first agents may be of the same type or different types such as anti-CD3 antibodies or fragments thereof or antigens bound to MHC molecules.

In some embodiments, the method of activating T cells further comprises the addition of a T-cell co-stimulator. Examples of T-cell co-stimulators include ligands targeted towards T-cell co-stimulatory receptors such as CD28, CD2, ICOS, OX40, or 4-IBB receptors. Suitable ligands may include one or more of natural or modified peptides, proteins (for example antibodies, affibodies), non-natural peptide mimics, nucleic acids (for example polynucleotides, PNA, DNA, RNA, or aptamers), polysaccharides (for example lectins, sugars), lipids, enzymes, enzyme substrates or inhibitors, ligands, receptors, antigens, or haptens. The addition of a T-cell co-stimulator may include the addition of one or more types of T-cell co-stimulators. In some embodiments the T-cell co-stimulator may be attached to a second binder moiety. The term "second binder moiety" refers to a molecule that can associate with one or more capture oligomers. In some embodiments, the second agent is a nucleic acid polymer and the second binder moiety is a nucleic acid sequence, which is same as or different from the nucleic acid sequence of the first binder moiety. In some other embodiments the second agent is a cationic polymer and the second binder moiety is an anionic moiety. In still other embodiments the second agent is an anionic polymer and the second binder moiety is a cationic moiety.

The term "attached" refers to any means of attachment known in the art. A T-cell activator can be attached to a first binder moiety by any means provided the attachment does not interfere with the activator's ability to activate T cells. Similarly, a T-cell co-stimulator can be attached to a second binder moiety by any means provided the attachment does not interfere with the co-stimulator's ability to provide a co-stimulatory signal to the T cell. The attachment may be covalent or noncovalent, electrostatic, or hydrophobic. In a preferred embodiment the attachment is covalent.

In a preferred embodiment the T-cell activator is an anti-CD3 antibody attached to a nucleic acid sequence, the T-cell co-stimulator is an anti-CD28 antibody attached to a nucleic acid sequence, and the second agent is a rolling circle amplification product comprising a plurality of complementary capture oligonucleotide sequences.

In preferred embodiments the first agent and the second agent are soluble in cell culture media. As to be understood, "cell culture media" refers to any standard T cell culture media, which are known in the art. Illustrative media include but are not limited to RPMI 1640, AIM-V, DMEM, MEM, α-MEM, F-12, X-Vivo 15. The T cell culture media may be serum-free or supplemented with serum, such as human serum or serum supplement. In some embodiments, the T cell culture media is further supplemented with additional growth factors and cytokines such as interleukin-2 (Il-2), interleukin-7 (Il-7) or interleukin-15 (IL-15).

As used herein, the term "in situ" generally refers to an event occurring in the original location, for example in the location where T cell activation occurs. In some embodiments "in situ" refers to an event happening in the T cell culture media under cell culturing condition.

The invention includes embodiments that relate generally to methods of activating T cells for cellular therapy. In some embodiments, the method includes the addition of a plurality of first agents, each first agent comprising a T-cell activator attached to a first binder moiety, wherein the T-cell activators are capable of binding to a set of T-cell surface receptors, such as the T-cell activating receptors, inducing a cellular event within the T cells that leads to activation and proliferation of the cells. In some embodiments a clustering of the T-cell surface receptors is induced by a second agent, which associates with the first binder moiety bringing the T-cell activators in proximity to each other. In some embodiments, the method further includes the addition of a plurality of T-cell co-stimulators capable of binding to a different set of T-cell surface receptors, such as the T-cell co-stimulatory receptors. The T-cell co-stimulator may be attached to a second binder moiety. The second agent associates with both the first binder moiety and the second binder moiety thereby inducing a clustering of the T-cell surface receptors. In some embodiments the second agent is a nucleic acid polymer comprising a plurality of capture oligonucleotide sequences and the association is caused by base-pair hybridization between a nucleic acid sequence attached to the T-cell activator and a complementary capture oligonucleotide sequence. In some embodiments the method further comprises the addition of a T-cell co-stimulator attached to a second binder moiety, wherein the second binder moiety is also a nucleic acid sequence, and the nucleic acid sequence is capable of association with a complementary capture oligonucleotide sequence by base-pair hybridization. In some embodiments the association of the capture oligomer with the first binder moiety and the second binder moiety is caused by electrostatic interaction between oppositely charged species for example anionic moieties attached to the T-cell activator and T-cell co-stimulator with cationic capture oligomers or vice versa.

In some embodiments, the first agent, the second agent, and optionally a T-cell co-stimulator, which may or may not be attached to a second binder moiety, are added simultaneously or sequentially in any order, to a population of T cells provided in a cell culture media, to allow an in-situ association. In still other embodiments, the first agent, the second agent, and optionally a T-cell co-stimulator attached to a second binder moiety, are allowed to pre-incubate and associate to form a pre-associated complex. The pre-associated complex is then added to the population of T cells. In preferred embodiments, the first agent, the second agent, and optionally the T-cell co-stimulator attached to a second binder moiety, are allowed to associate in-situ.

The T cells are incubated with the first agent, the second agent, and optionally a T-cell co-stimulator for a period of time, whereby at least a portion of the population of T cells is activated. In some embodiments the T-cell co-stimulator is attached to a second binder moiety. In some embodiments the time sufficient to activate a portion of the population of T cells may range from about 1 minute to about 14 days. In certain embodiments, the time may be from about 24 h to about 8 days. In some embodiments, at least 15% of T cells are activated. In preferred embodiments at least 25% of the T cells are activated, and in more preferred embodiment the majority of the T cells, greater than 50% are activated. The incubation may be done in a bioreactor having a controlled environment of temperature, humidity, CO2 concentration, for example at 37° C. and 5% CO2. In some embodiments the incubation may be done in a static bioreactor where there is no movement of the bioreactor, while in some other embodiments the incubation may be done in a bioreactor placed on a rocking platform.

In some embodiments the invention provides methods to activate and selectively expand a specific subpopulation of T cells from a mixed population of T cells. This can be achieved for example by varying the nature or relative proportion of the T-cell activators and T-cell co-stimulators. Further, the invention provides methods to control T-cell surface receptor clustering and hence activation by adjusting for example the number of or distance among the T-cell activators and T-cell co-stimulators, which are associated with the second agent. In an exemplary embodiment where the second agent is a nucleic acid polymer, this can be achieved by precisely controlling the number and/or length of the capture oligonucleotides, or the length of the spacers.

The expression of certain antibodies such as CD25 may be used to measure the activation of the T cells. In certain embodiments the expression of CD25 receptors on the T cells may be assayed by labeled anti-CD25 antibodies to enumerate the labeled cells. In certain other embodiments, activation may be measured by other markers signifying T-cell surface receptor clustering, which induces activation and expansion. The other markers used to measure T cell activation and expansion include CD4, CD8, CD27, CD28, CD3, CD57, CD25, and CD62L.

In preferred embodiments, the first agent and the second agents are bio-degradable. As used herein, the term bio-degradable refers to materials that degrade in biological fluid. In some embodiments, the degradation may occur using chemical or enzymatic means. In some embodiments, where the second agent is a nucleic acid polymer and/or the first binder moiety is a nucleic acid sequence, the method of activation of T cells further comprises the addition of a degrading enzyme such as a nuclease. In some embodiments the degrading enzyme, such as the nuclease, is added after at least a portion of the population of T cells is activated. In some embodiments, the degrading enzyme is added after the T cells have expanded at least 10-100 fold. In still other embodiments, the degrading enzyme is added at the end of the culture period, before the T cells are harvested from the cell culture media, prior to washing, concentration and final formulation. It should be noted that the degrading enzyme can be added any time after at least a portion of the population of T cells is activated and before the T cells are administered into a patient. In certain embodiments, after degradation, the degraded by-products of the first and second agents can be removed during washing and concentration of the T cells, and additional purification steps are not necessary. In some other embodiments, the second agent and the first agent are biocompatible and may be rapidly degraded in the blood stream. In such cases, the addition of a degrading enzyme may not be required before the T cells are administered into a patient. The use of such soluble, biodegradable systems are advantageous over polystyrene beads or other comparable bead based approaches since the use of such systems may avoid the need for additional purification steps, such as magnetic separation, which often leads to significant cell loss. In embodiments that include the addition of a T-cell co-stimulator attached to a second binder moiety, the second binder moiety is also biodegradable.

In some embodiments, the method of T cell activation further comprises the addition of a vector comprising a foreign gene. In some embodiments the foreign gene encodes a chimeric antigen receptor or a T-cell receptor. In some embodiments, the vector is a viral vector such as a γ-retroviral vector or a lentiviral vector. In some other embodiments the vector is a plasmid vector. In some embodiments the vector is added simultaneously with the first agent, while in some other embodiments, the vector is added after at least a portion of the population of T cells is activated.

Some embodiments are directed towards a kit comprising a T-cell activator attached to a nucleic acid sequence, a nucleic acid polymer comprising a plurality of capture oligonucleotide sequences, and optionally a T-cell co-stimulator. In some embodiments the T-cell co-stimulator is attached to a nucleic acid sequence, which is same as or different from the nucleic acid sequence attached to the T-cell activator. In specific examples the kit is a DNA-Based T cell Activation (DBTA) construct comprising a DNA polymer such as a rolling circle amplification product and one or more of the following components, i) a T-cell activator attached to a DNA sequence (first binder moiety), and ii) a T-cell co-stimulator attached to a DNA sequence (second binder moiety), which is same as or different from the DNA sequence attached to the T-cell activator.

EXAMPLES

The following examples are intended only to illustrate methods and embodiments in accordance with the invention, and as such should not be construed as imposing limitations upon the claims.

Example 1: Synthetic Preparation of DNA Attached Antibody (Ab-DNA) Conjugates for T Cell Activation DNA-Based T cell Activation (DBTA) polymer constructs are representative nucleic acid polymer systems that initiate T cell clustering, activation, and subsequent expansion. DBTA comprises a DNA polymer produced via rolling circle amplification (such as RCAact) and consisting of repeating 43-base oligonucleotide segments and one or more of the following components: (1) anti-human CD3 monoclonal antibodies conjugated to 20-base DNA sequence derived from human beta-actin (o20b(+)act), (2) anti-human CD28 monoclonal antibodies also conjugated with DNA sequence o20b(+)act. The 43-base oligonucleotide segments bear full complementarity to the DNA sequences conjugated to the antibodies (1) and (2). The sequences of RCAact are derived from the complement to the RCA template sequences given below in Table 1:

Synthesis of Anti-CD3-DNA and Anti-CD28-DNA Conjugates

The covalent attachment of DNA sequences to antibodies (Abs) proceeds via a maleimide-thiol coupling strategy as described below. The following specific description of anti-CD3-o20b(+)act and anti-CD28-o20b(+)act conjugate synthesis, purification, and characterization can be adapted as a general conjugation strategy for different antibody (Ab) clones as well as nucleic acid sequences of different length and composition.

Preparation of Maleimide-Activated DNA Sequences

The starting nucleic acid sequence (prot-mal-o20b(+)act) is provided by TriLink Biotechnologies and comprises a 20-base DNA sequence capped with an N-terminal C6 spacer followed by a protected tricyclic maleimide moiety. Upon receipt of this commercial material, a reactive mal-o20b(+)act derivative is generated via an inverse electron-demand Diels-Alder deprotection step, whereby the starting nucleic acid sequence is suspended in anhydrous toluene (~1 mg/mL) and heated at 90° C. for 4 h. Precipitation of the nucleic acid sequences via benchtop centrifugation and removal of solvent is followed by several washes (3×1 mL) with cold ethanol. Upon further reduction of residual organic solvents under reduced pressure, the washed solid product is dissolved in 100 mM HEPES buffer, pH 7.3 and the solution concentration is determined via UV-Vis spectroscopy (NanoDrop). The resulting stock solution (0.5-1 mM in DNA) or a portion thereof may be used directly for antibody conjugation with thiol-modified antibody. The remaining mal-o20b(+)act stock may be stored for several months at −20° C. without significant loss of reactivity.

Preparation of Thiol-Modified Ab Intermediates.

A 10 mM stock solution of Traut's reagent (2-aminothiolane hydrochloride) is first prepared in 100 mM HEPES buffer, pH 7.3. A 1 mg/mL solution of anti-CD3 Ab (OKT3 clone, eBioscience) or anti-CD28 Ab (9.3 clone, GeneTex) in PBS is then mixed with both 20× pH 8.5 borate buffer (ThermoFisher) and 10 mM Traut's reagent stock solution in a 8:1:1 ratio by volume. The resulting solution is thoroughly mixed and allowed to incubate at room temperature for 0.75 h. The unused portion of the Traut's mixture may be stored for several months at −20° C. without significant loss of

TABLE 1

Modification key: Phos = 5' phosphate, Mal = maleimide functional group, C6 = hexylamino modification

| Name | sense | length (b) | Sequence (5'→3') including modifications | SEQ ID NO | use/application |
|---|---|---|---|---|---|
| RCA primer | - | 20 | TGA CTA TTA AGA CTT CCT GT | 1 | primer for RCA reactions, sequence derived from human beta-actin |
| RCA template (CpG) | + | 43 | /Phos/TTA ATA GTC ATT CCA AAT ATG AGA TGC GTT GTT ACA GGA AGT C | 2 | template for RCA reactions, sequence derived from human beta-actin and contains CpG island |
| RCA template (no CpG) | + | 43 | /Phos/TTA ATA GTC ATT CCA ACA TAT GAG ATG GTT GTT ACA GGA AGT C | 3 | template for RCA reactions, sequence derived from human beta-actin and does not contain CpG island |
| o20b(+)act | + | 20 | /MalC6/ACA GGA AGT CTT AAT AGT CA | 4 | conjugation to Ab via 5'-maleimide and binding to human B-actin-derived RCA product | reactivity. Following antibody activation, the reaction mixture is purified using a conventional desalting column (e.g. NAP-5 or PD-10, GE Healthcare Life Sciences) that has been equilibrated with 100 mM HEPES, pH 7.3 buffer. The collected fractions are then immediately analyzed by UV-Vis spectroscopy (NanoDrop). The resulting protein recovery at this stage is typically >60% for both anti-CD3 and anti-CD28 antibodies using known molar extinction coefficients for antibody at 280 nm.

Conjugation of Maleimide-Activated DNA Sequences with Thiol-Modified Ab Intermediates to Generate Ab-DNA Conjugates For the final Ab-DNA attachment step, the volume of mal-o20b(+)act corresponding to a target molar input ratio of 10-40:1 o20b(+)act:Ab is added to an aliquot of freshly prepared, purified, thiol-activated Ab. After thorough mixing, the resulting solution is allowed to incubate at room temperature overnight (16-24 h). Final conjugate purification is achieved via selective precipitation of Ab using a saturated ammonium chloride solution. First, a volume of saturated ammonium chloride equal to the total reaction volume is added, thoroughly mixed, and placed on ice. After 15 min, the sample is centrifuged at 15,000×g rcf for 10 min at 10° C. Removal of the supernatant is followed by addition of an appropriate minimum volume of 0.1M sodium phosphate, 0.15M NaCl, pH 7 buffer to re-dissolve the final pellet. The final antibody-DNA conjugate recovery and labeling efficiency (attached Ab-DNA) is determined using the Pierce BCA Protein Assay Kit (Thermo Scientific) in combination with NanoDrop A260 measurement for determination of DNA content ($\varepsilon=210,100$ $M^{-1}$ $cm^{-1}$). Under these condition an average of 1-3 o20b(+)act oligonucleotide molecules are conjugated to each molecule of anti-CD3 or anti-Cd28 antibody. Attachment is generally achieved with a final conjugate recovery of >60%. Further confirmation of conjugate purity is determined using analytical size exclusion chromatography (SEC) against a standard protein size calibration curve. Typical analytical SEC conditions are as follows: 10 μL sample injection volume, 0.5 mL/min flow rate, 30 min run using 100 mM sodium phosphate, 100 mM sodium sulfate, 0.05% sodium azide, pH 6.7 buffer on a TSK Gel 3000SWxL column (TOSOH Bioscience). Typical analytical SEC elution times are as follows: unlabeled Ab=16.8-17.0 min, starting o20b(+) act=20.0 min. Ab-DNA (Ab-o20b(+)act) conjugate mixture=10-15 min. Purified final Ab-DNA conjugates (after precipitation and resuspension) show >95% removal of unbound DNA intermediate or starting material upon SEC analysis.

Example 2: Validation of T Cell Binding for Anti-CD3-DNA and Anti-CD28-DNA Conjugates To ensure that the Ab-DNA conjugates prepared in Example 1 retain their specific cell binding capabilities to T cells, validation studies are performed for each conjugate batch using flow cytometry (Cytoflex S, Beckman Coulter). NBP Pan T Cells (ALL Cells) are thawed at 37° C. in 10 mL warm complete media (see Example 4) and then centrifuged at 300×g rcf for 10 min. Cells are then resuspended in 10 mL fresh complete media and analyzed on a Nucleocounter® NC-200 system to determine cell counts and viability. After adjusting the concentration to $1\times10^6$ cells/mL and washing with PBS, the T cells are then blocked in 10% Normal Goat Serum (NGS) in PBS at 4° C. for 15 min. After removal of the blocking solution, cells are then incubated with primary antibody in 1% NGS/PBS solutions for 15 min at 4° C. In parallel, both anti-CD3-DNA and/or anti-CD28-DNA conjugate (anti-CD3-o20b(+)act and/or anti-CD28-o20b(+)act) test samples (Example 1) as well as unlabeled or unconjugated anti-CD3 and/or anti-CD28 Ab positive controls (Ab not attached to DNA) are used. After primary Ab incubation, cells are washed in PBS and incubated with a 1% NGS/PBS solution of fluorophore-labeled secondary antibody (Jackson Immuno) specific for the mouse isotype of both anti-CD3 and anti-CD28 Abs. Typical dilutions for secondary antibody labeling are 1:200 of a 1 mg/mL stock solution. After 15 min incubation at 4° C., cells are washed as before, resuspended in PBS and analyzed by flow cytometry to determine the percentage of T cells bound with Ab-DNA conjugate relative to the percentage of cells bound with unlabeled Ab (positive control).

Representative flow cytometry histograms for positively validated anti-CD3-o20b(+)act and anti-CD28-o20b(+)act conjugates binding to T cells are shown in FIG. 1A through 1E; Anti-CD28-o20b(+)act, anti-CD28 unlabeled, Anti-CD3o20b(+)act, anti-CD3 unlabeled, and FITC-labeled respectively. For these particular Ab-DNA conjugate batches, high percentage of anti-CD3+ and anti-CD28+ cell binding is observed (>85% for both). These results indicate that despite DNA attachment, a significant portion of the anti-CD3 and anti-CD28 Ab samples retain their T cell binding capabilities.

Figure 2:
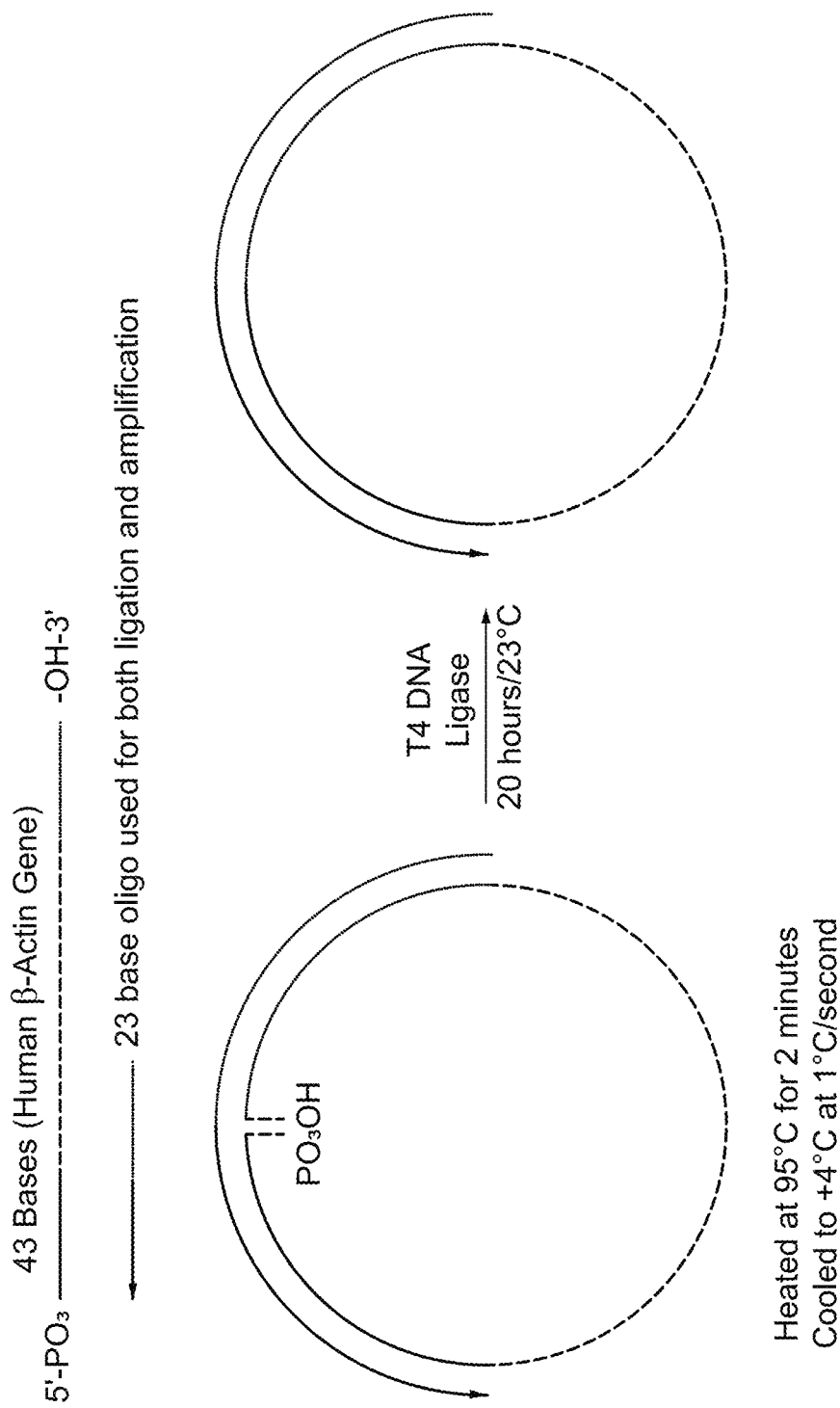
FIG. 2 is an illustration of the preparation of single stranded rolling circle amplification (ssRCA) to produce RCA products (RCAact) for T cell activation in two steps.

Example 3: Production of a Nucleic Acid Polymer for T Cell Activation Using Rolling Circle Amplification Preparation of single stranded rolling circle amplification (ssRCA) to produce RCA products (RCAact) for T cell activation comprises two steps: 1) ligation of a linear DNA strand to generate a circular template, and 2) amplification of the ligated circle to synthesize long single stranded concatemers. The ligation was accomplished using a high concentration of T4 DNA Ligase and its corresponding reaction buffer (New England Biolabs®) Two deoxyoligonucleotides (oligonucleotide) were present in the ligation. One oligonucleotide (RCAact-NoCG) consisted of 43 bases of the DNA sequence of the human β-actin gene and contained a 5' phosphate group. This 43 base oligonucleotide would become the circular template following ligation. The second oligonucleotide was 20 bases in length (RCAact Primer) and was complimentary to both ends of the 43 base oligonucleotide. This second oligonucleotide was used to both form the circle prior to ligation and then amplify the circle in the subsequent ssRCA reaction (see FIG. 2). 450 pmol of the 43 base oligonucleotide were mixed in a 120 μL volume with 300 pmol of the 20 base oligonucleotide in an annealing buffer consisting of 10 mM Tris, pH 8, and 50 mM sodium chloride. The mixture was heated at 95° C. for two minutes and then cooled to +4° C. by dropping the temperature 0.1° C. every second. After cooling the mixture was warmed to room temperature and 96 μL of this annealing reaction was mixed with 48 μL of 10× T4 DNA Ligase Buffer containing 10 mM ATP and 24 μl of T4 DNA Ligase (400 units/μl) in a final volume of 480 μL. The ligation reaction was allowed to incubate at 23° C. for 20 hours and then 65° C. for 20 minutes to heat-kill the ligase.

The ssRCA reaction was prepared by mixing 69.3 μL of the completed ligation reaction with 550 μL of 2× Phi29 Reaction Buffer (100 mM HEPES Buffer, pH 8.0, 150 mM potassium chloride, 2 mM TCEP, 40 mM magnesium chloride, 0.02% (v/v) Tween 20, 5% (v/v) polyethylene glycol and 1.6 mM each dATP, dCTP, dGTP and dTTP) in a final volume of 1.078 mL. After mixing, amplification was started by the addition of 22 μL of 1 mg/ml Phi29 DNA polymerase. Amplification reactions were incubated at 30° C. for 18 hours and then 65° C. for 15 minutes to heat-kill the polymerase. Completed ssRCA reactions were split equally into three separate tubes and precipitated by the addition of 0.1 volume 3M sodium acetate and 2.5 volumes of 95% (v/v) ethanol. Precipitations were allowed to stand at room temperature for 30 minutes and then centrifuged at high speed (>20K×g) for 30 minutes. The supernatants were removed by aspiration, each DNA pellet rinsed with 500 μl of 70% (v/v) ethanol and then recentrifuged at high speed (>20K×g) for 5 minutes. The supernatants were again removed by aspiration and the DNA pellets resuspended in TET Buffer (10 mM Tris, pH 8.0, 0.1 mM EDTA and 0.01% (v/v) Tween 20).

The apparent size of RCAact products is determined by pulse field gel electrophoresis relative to yeast (*S. cerevisiae*) or lambda DNA molecular weight ladders. In addition to pulse-field analysis, gel-shift assays using non-denaturing agarose gels are used to confirm hybridization of anti-CD3-o20b(+)act and anti-CD28-o20b(+)act conjugates (Example 1) with RCAact.

Example 4: Comparison of T Cell Activation and Expansion Using Dynabeads® Human T-Expander CD3/CD28 and a DBTA System of Nucleic Acid Polymers with Ab-DNA Conjugates (Anti-CD3-DNA and Anti-CD28-DNA)

Frozen aliquots of human Pan T Cells from AllCells (Catalog# PB009-IF) are used for all activation and expansion studies. Pan T Cells are thawed and processed as described in Example 2 and added to following complete X-Vivo media to give an initial concentration of 1×106 cells/mL as shown in Table 2.

TABLE 2

X-Viro media aliquots

| Component | Vendor | Cat# | Final concentration in media | Volume (ml) |
|---|---|---|---|---|
| Human serum off the clot | Valley Biomedical | HS1017 | 5% | 50 |
| Glutamax 1-CTS | Gibco | A12860-01 | 1% | 10 |
| Pen-Strep | ThermoFisher | 15140-122 | 1% | 10 |
| N-acetyl cysteine | Sigma | A9165 | 0.8% | 8 |
| IL-2 | Thermo Fisher | 200-02 | 200 IU | 0.152 |
| X-Vivo media | Lonza | BE04-743Q | 92% | 1000 |

Typical activation and expansion experiments are performed in a 6-well format using a 2 mL seeding volume per well with a minimum of one additional replicate per condition tested. Dynabeads® Human T-Expander CD3/CD28 (Catalog#111.41D, ThermoFisher) are prepared according to the manufacturer's instructions. Briefly, a bead aliquot is washed with 0.3 mL complete media three times, with supernatant wash removal occurring after sample application to DynaMag-2 permanent magnet (ThermoFisher). After resuspension in complete media, a 60 μl bead slurry aliquot is added per well such that an approximate 3:1 bead-to-cell ratio is used for initial activation conditions (starting with 2×10$^6$ total cells per well).

Figure 3A:
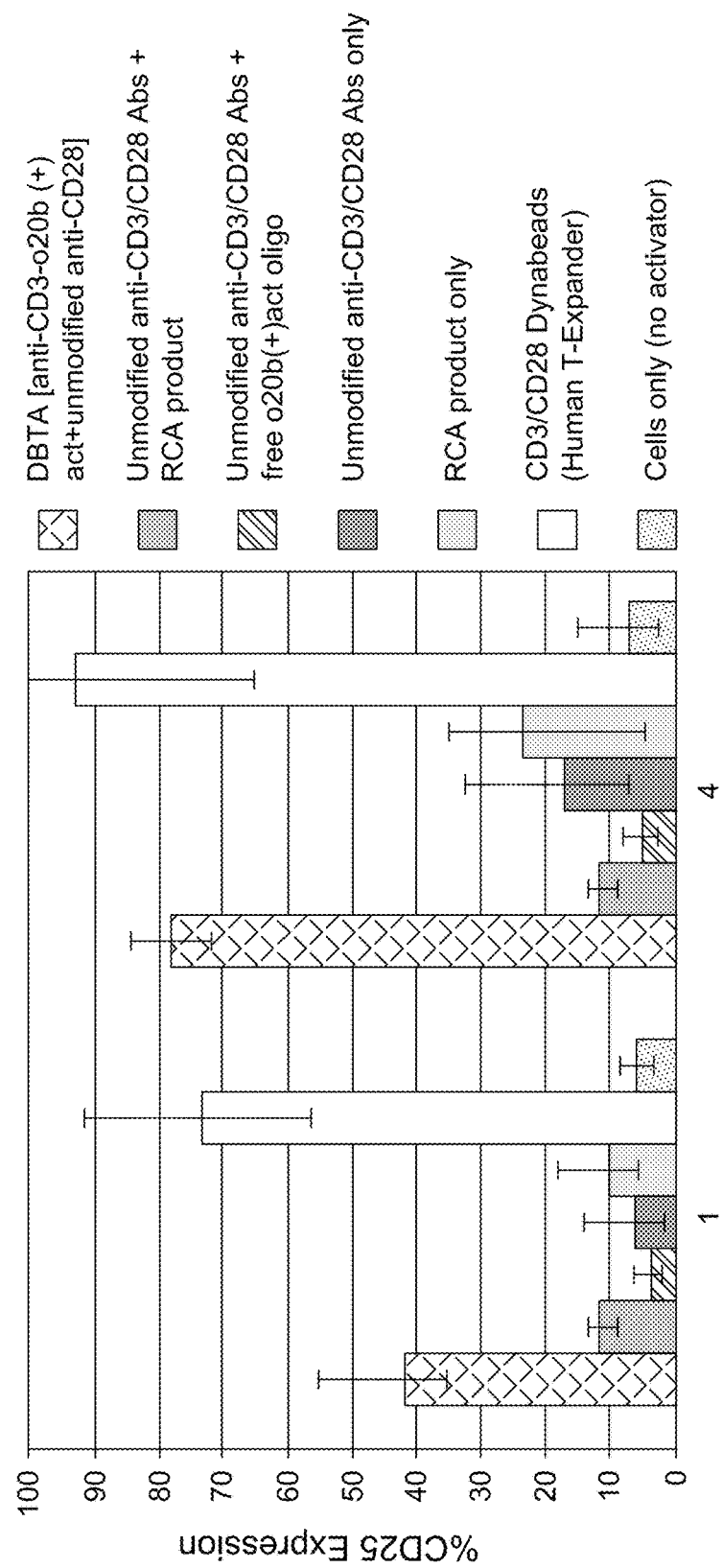
FIG. 3A is graphical representation of T cell activation measured as population of cells expressing CD25 receptor (a marker of T cell activation) by DBTA (DNA-Based T cell Activation) relative to the CD3/CD28 Dynabeads benchmark with respect to both early (days 1 and 4) % CD25 expression. Also shown are various controls including unconjugated antibodies alone and cells alone (without activator) not expected to cause significant activation.
Figure 3B:
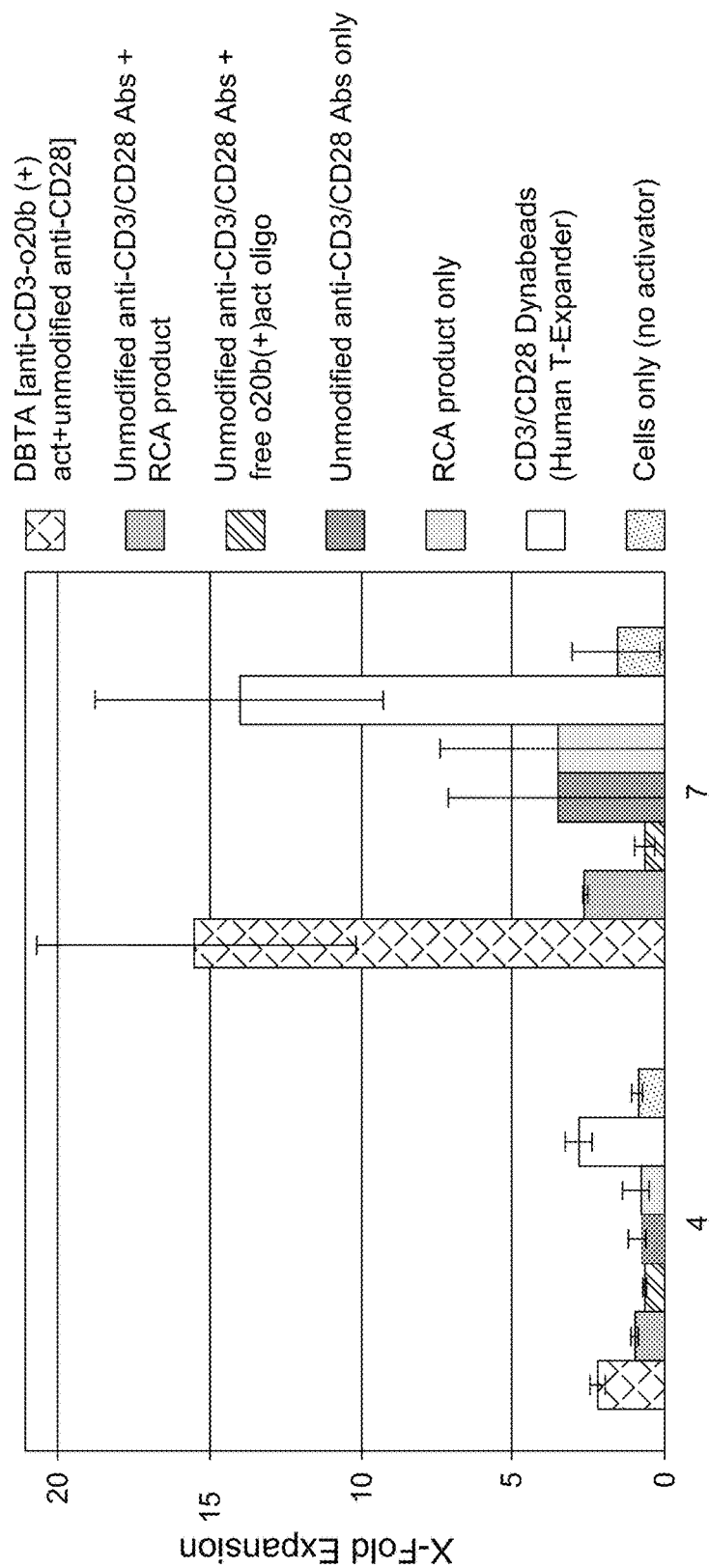
FIG. 3B is a graphical representation of the same cultures as in FIG. 3A at days 4 and 7 showing cell expansion represented as number of folds of expansion relative to starting count (cell counts).
Figure 4A:
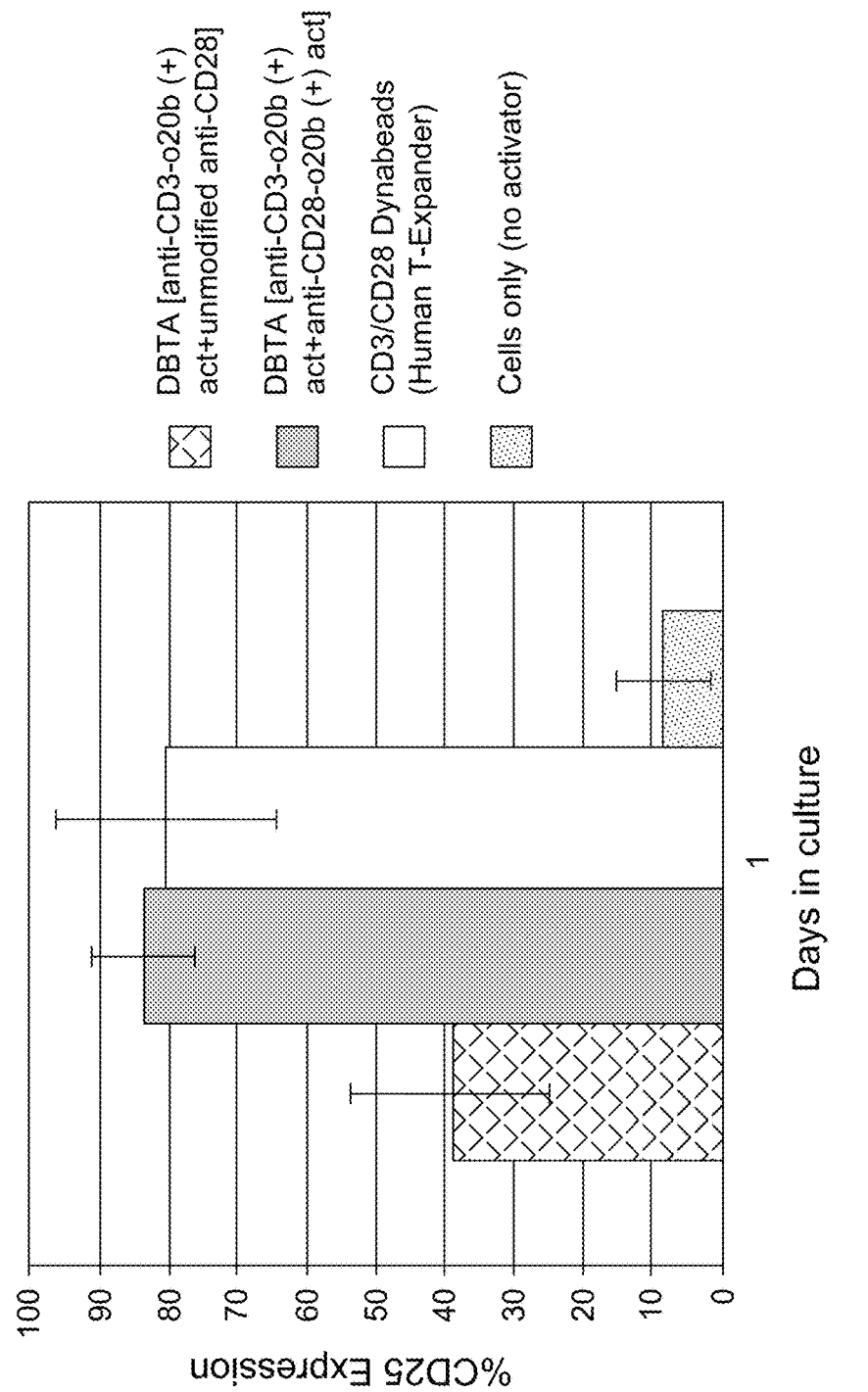
FIG. 4A is a graphical representation showing significant activation (relative to control) achieved with different DBTA systems, a DBTA system wherein only the anti-CD3 antibody is attached to the o20b(+)act (anti-CD3-o20b(+)act) and another DBTA system wherein both anti-CD3 and anti-CD28 are attached to o20b(+)act. Measured is the % CD25 expression.
Figure 4B:
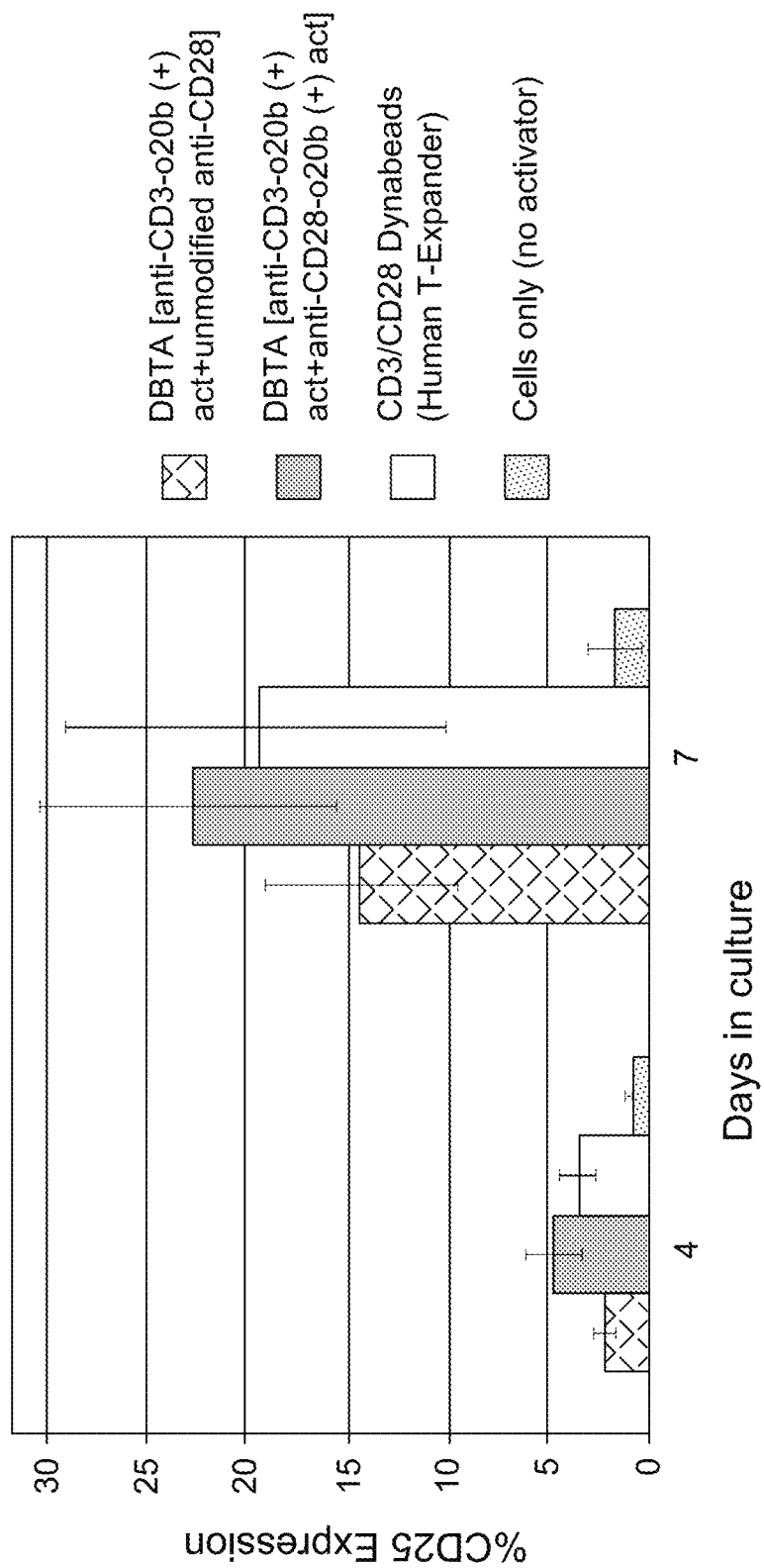
FIG. 4B is a graphical representation of the same cultures as FIG. 4A after 4 and 7 days showing x-fold expansion (cell counts) as in FIG. 3B.

Unless otherwise specified, aliquots of DBTA components (Ab-DNA and RCAact) are added separately and consecutively to cells directly from their respective stock solutions (stored at 4° C.). Additions of each DBTA component may be made in any sequential order. Standard initial concentrations of DBTA components are as follows: 1 μg/mL (6.7 nM) each for anti-CD3-o20b(+)act (anti-CD3-DNA) and anti-CD28-o20b(+)act (anti-CD28-DNA) with 10-fold molar excess of RCAact (~67 nM). RCAact concentration is based on the molar concentration of the repeating 43-base segment and independent of total RCA product length or polydispersity. Following the addition of all of the appropriate activating components, the well contents are mixed with a 1 mL pipette. The plates are then incubated at 37° C. and 5% CO2 atmosphere under static conditions for 1-7 days or longer with periodic aliquots taken and, dilutions done with fresh media as needed for continuing expansion and analysis. Confirmation of cell activation is achieved by % CD25 expression using flow cytometry after 24 h incubation (day 1) and followed by additional measurements, if needed, at days 4 and 7. Cell counts, viability, and size (blasting) are additionally measured at days 4 and 7 using the Nucleocounter. Based on day 4 cell counts, a 1:4 or 1:8 dilutions with fresh complete media is performed to reduce cell density to 250,000 cells/mL per well. This enables cells to expand in the exponential phase, without overgrowth, until day 7 analysis. For the negative control ("cells-only") sample group in which no activating agents are added, cell density is maintained at a minimum of 500,000 cells/mL. Further phenotypic analysis via flow cytometry may be conducted at day 7 for select samples of interest. The panel of cell surface markers under investigation includes CD4, CD8, CD27, CD28, CD3, CD57, CD25, and CD62L. FIGS. 3A and 3B shows clear, comparable performance of DBTA relative to the CD3/CD28 Dynabeads benchmark with respect to both early (days 1 and 4) % CD25 expression as well as x-fold cell expansion after days 4 and 7. Control samples with unmodified antibodies, RCA alone, unmodified antibodies with unconjugated nucleic acid sequence (free oligo) and cells only show very low level of activation and expansion, as expected. The robustness of the DBTA system is also confirmed as the standard deviations of activation and expansion match those observed with Dynabeads. FIGS. 3A and 3B includes data from five separate experiments, seven individual human T cell donors, and 4 different batches of antibody conjugates. FIGS. 4A and 4B show that significant activation and expansion (relative to control) can also be achieved with a DBTA system wherein only the anti-CD3 antibody is attached to the o20b(+)act (anti-CD3-o20b(+)act). FIG. 4A shows the CD25 expression of the cultures after 24 hrs while FIG. 4B shows the CD25 expression of the same cultures after 4 and 7 days of expansion. However, the best performance is achieved when both anti-CD3 and anti-CD28 antibodies are attached to DNA to form the Ab-DNA conjugates. The data for FIG. 4 represents averages taken from over 5 separate experiments encompassing over six individual human T cell donors.

Example 5: Comparison of Large-Scale T Cell Activation and Expansion Using Dynabeads® (ThermoFisher Scientific, Waltham, Mass.) Human T-Expander CD3/CD28 and a DBTA System of Nucleic Acid Polymers (RCAact) with Ab-DNA Conjugates (Anti-CD3-o20b(+)Act and Anti-CD28-o20b(+)Act)

In addition to 6-well plate studies, a large scale comparison of T cell activation and expansion efficiency using 72C VueLife® bags (Cell Genix GmbH, Breisgau, Germany)

was also undertaken. The same ratios and components described in Example 4 were scaled linearly to accommodate starting conditions of 32×10⁶ cells in 32 mL of complete X-Vivo media (1×10⁶ cells/ml). The cultures were maintained in the 72C VueLife bags within a standard cell culture incubator. On Day 4, cells were collected, washed with fresh media, counted, diluted in appropriate media volume to give 0.5×106 cells/mL and re-seeded within the VueLife 72C. On Day 6, cells were diluted and seeded in 250 mL in the Wave bag, on a rocking WAVE platform for further expansion. By Day 8, cells were counted using Nucleocounter® (ChemoMetec, Allerod, Denmark) and examined by flow cytometry for various CD surface marker expression. The tables below depict comparable levels of CD25 expression, x-fold expansion, cell size, and viability for both Dynabead samples and those activated with DBTA. In addition, the day 8 flow analysis shows nearly identical levels of phenotypic expression for the full panel of CD markers for both Dynabeads and DBTA. The preparation and results are illustrated in Tables 3-5 below.

TABLE 3

Cell Counts at 4 and 8 days.

| Sample | % CD25 (24 h) | Cell counts | | | Fold X | |
|---|---|---|---|---|---|---|
| | | Day 4 (cells/ml) | Day 4 (total viable cells) | Day 8 (cells/ml) | Day 4 | Day 8/ Day 6 |
| DBTA | >90% | 8.45E+05 | 4.23E+07 | 1.57E+06 | 1.32 | 6.04 |
| Dynabeads | >90% | 1.25E+06 | 6.25E+07 | 1.38E+06 | 1.95 | 5.31 |

TABLE 4

Cell Viability as a percentage of population.

| Sample | Day 8 total Viable Cells | Cell size (µm) | | % Viability | |
|---|---|---|---|---|---|
| | | Day 4 | Day 8 | Day 4 | Day 8 |
| DBTA | 3.93E+08 | 12.2 | 10.9 | 98.1 | 97.5 |
| Dynabeads | 3.45E+08 | 12.1 | 11.0 | 97.6 | 97.1 |

TABLE 5

Cell Flow Cytometry results at 8 days.
Flow Cytometry Results at day 8
(% cells positive):

| CD Marker | DBTA | Dynabeads |
|---|---|---|
| CD8 | 46% | 45% |
| CD4 | 51% | 53% |
| CD3 | 96% | 98% |
| CD25 | 80% | 84% |
| CD57 | 10% | 8% |
| CD62L | 95% | 96% |
| CCR7 | 62% | 47% |
| CD28 | 96% | 95% |
| CD27 | 98% | 96% |
| CD27⁺CD28⁺ | 90% | 82% |

Example 6: The Effect of Pre-Incubating DBTA Components Together Prior to Cell Culture Addition Versus Simultaneous Addition of all Components at the Start of Activation A series of T cell activation experiments were conducted to assess the effect of pre-incubating all of the DBTA system components (Anti-CD3-DNA and anti-CD28-DNA conjugates along with their complementary RCAact polymeric product) and then adding the pre-associated complex to T cells. The results were compared to the standard protocol of simultaneous addition of each separate component to T cells for in-situ association. For these pre-incubated samples, the same quantities and ratios of DBTA components used in Example 4 were added together in a 1.5 mL tube, mixed thoroughly, and incubated at room temperature for 30 minutes. The pre-incubated DBTA mixture was then added to fresh T cell cultures in the 6 well plates. In parallel, and as conducted in Example 4, standard DBTA samples not subjected to pre-incubation were added to T cell cultures along with standard Dynabead and cells only samples (positive and negative controls, respectively).

Figure 5A:
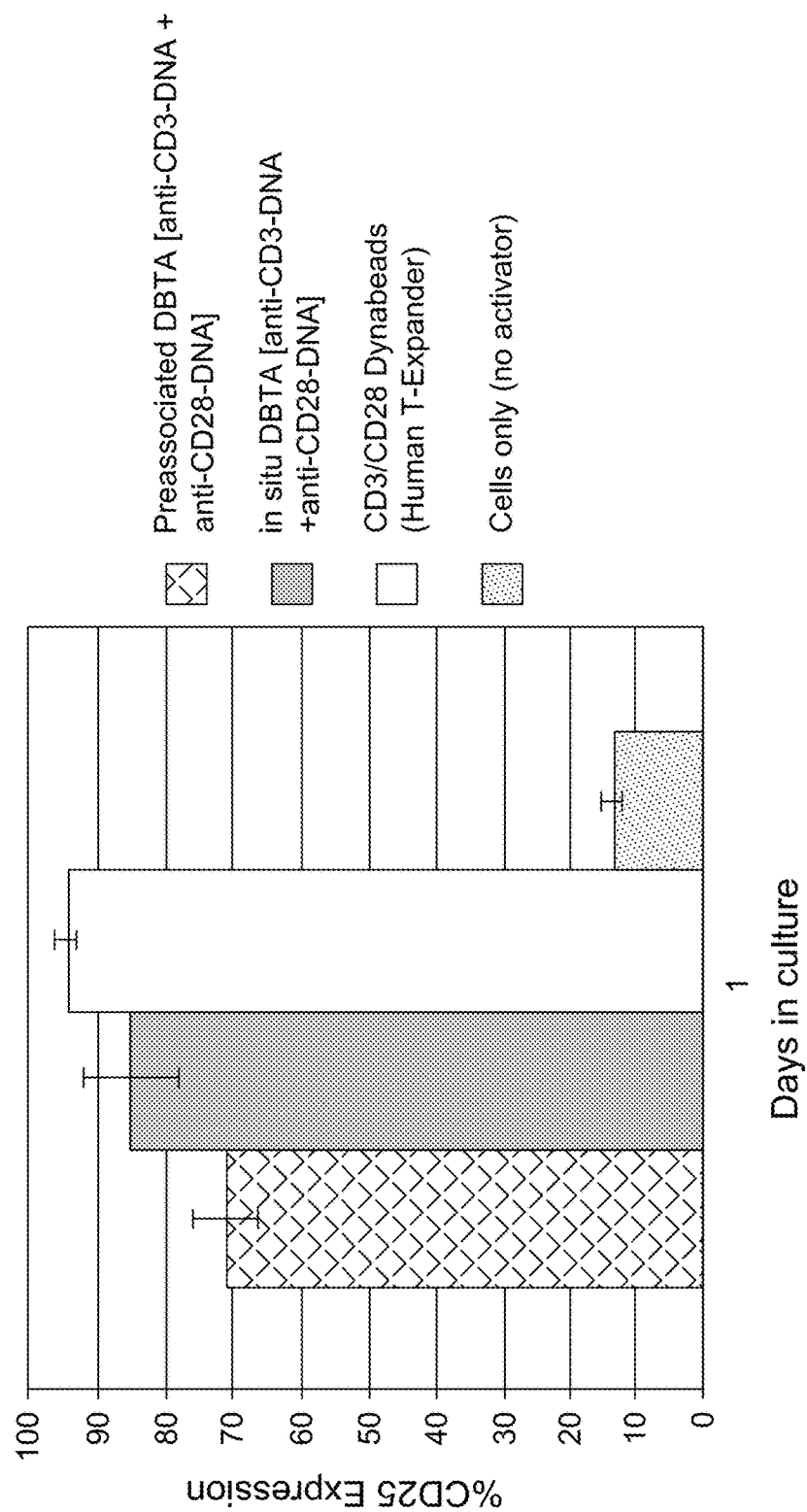
FIG. 5A is a graphical representation showing a trend towards higher activation when the DBTA components are mixed in situ compared to when they are pre-incubated/pre-associated and then mixed with cells.
Figure 5B:
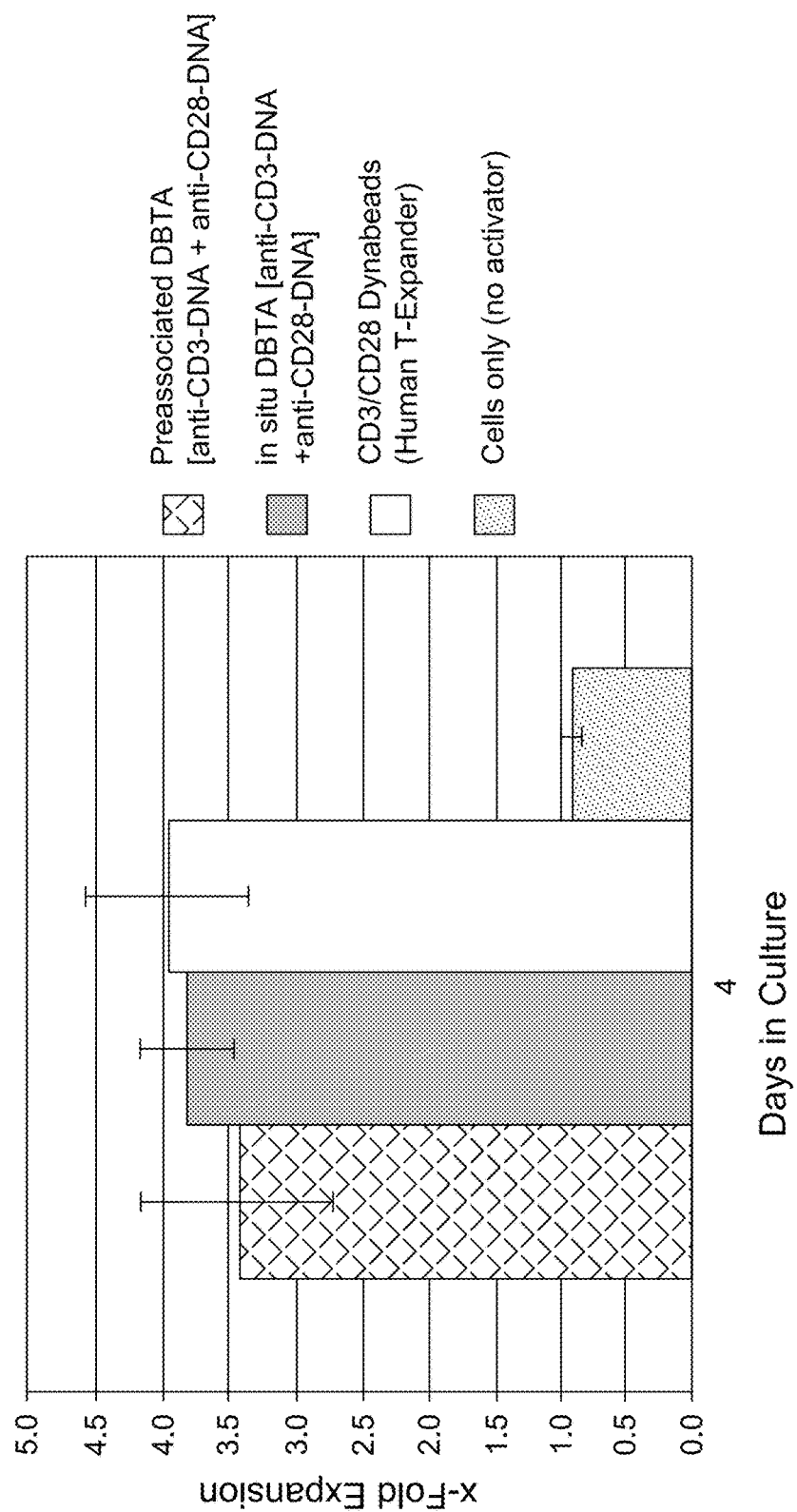
FIG. 5B is the same cultures as FIG. 5A after 4 days showing x-fold expansion (cell counts).

FIGS. 5A and 5B shows that comparable levels of both early activation (24-hour % CD25 expression) and day 4 cell expansion is achieved whether or not the all the DBTA components are pre-incubated/pre-associated (anti-CD3-DNA/anti-CD28-DNA DBTA pre-associated) together or added simultaneously at the start of cell activation (anti-CD3-DNA/anti-CD28-DNA DBTA in-situ) FIG. 5A is after 24 hr incubation and 5B is after 4 days. Both sets of DBTA samples likewise compare favorably to benchmark Dynabead numbers for activation and early expansion. This data is derived from two separate experiments featuring four different human T cell donors and four different batches of Ab-DNA conjugates.

Example 7: The Effect of Different Input DBTA Antibody Conjugate and RCA Polymeric Product Quantities on T Cell Activation Efficiency A series of T cell activation experiments were conducted to assess the effect of different ratios of Ab-DNA conjugate and RCAact on T cell activation efficiency. In all cases, the same anti-CD3-DNA:RCAact molar ratio of 1:10 was maintained, while 1:1 versus 1:2 molar ratios of anti-CD3-DNA: anti-CD28-DNA conjugate were examined. All other protocol conditions outlined in Example 4 were maintained.

Figure 6A:
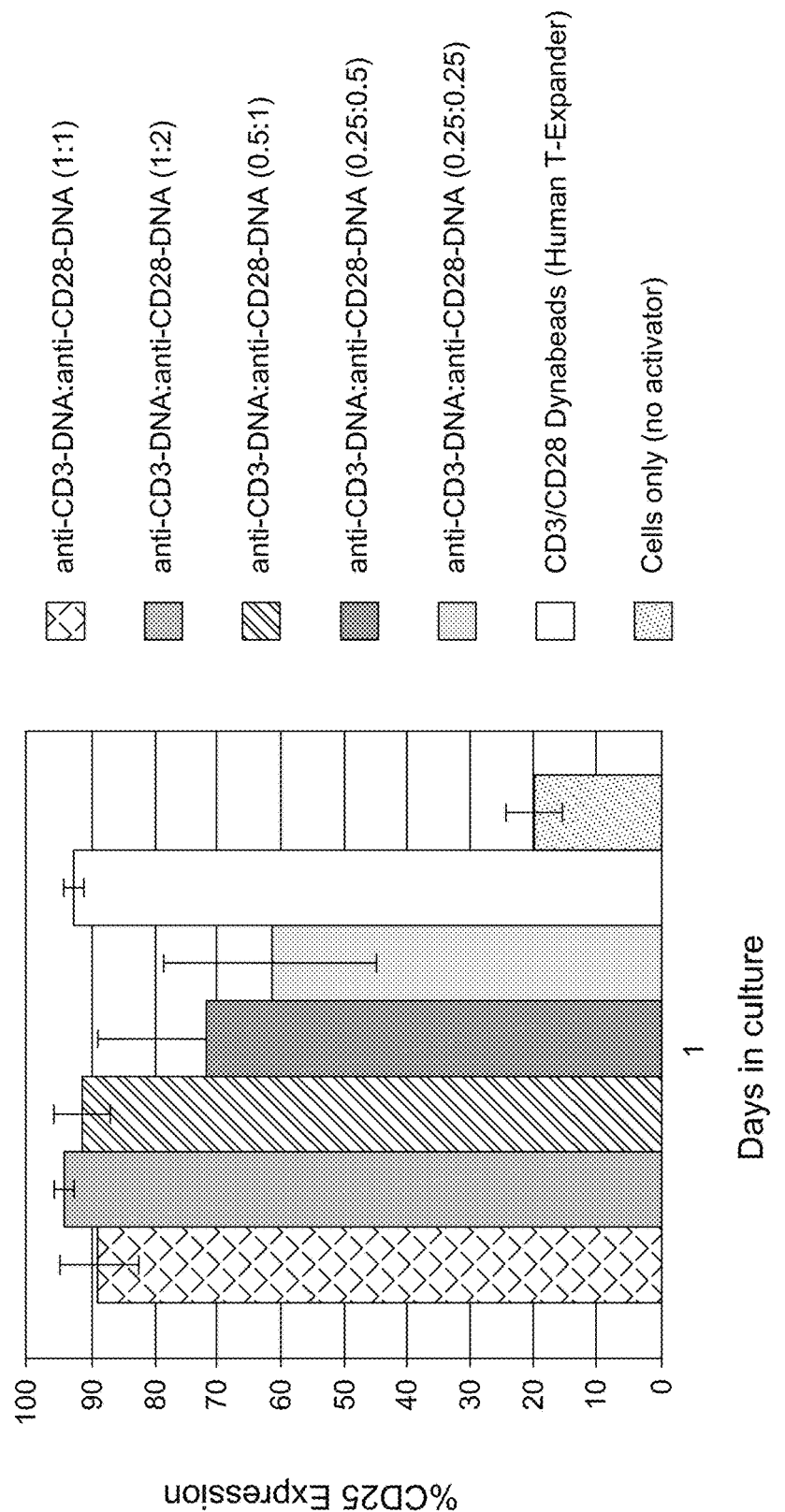
FIG. 6A is a graphical representation showing T cell activation (24-hour % CD25) under a variety of conditions including different ratios of anti-CD3-DNA and anti-CD28-DNA with same RCA amount (10 RCA repeat units/per anti-CD3-DNA conjugate) and different amounts of DBTA reagent while keeping the ratio of anti-CD3-DNA conjugate and RCA repeat unit constant at 1:10.
Figure 6B:
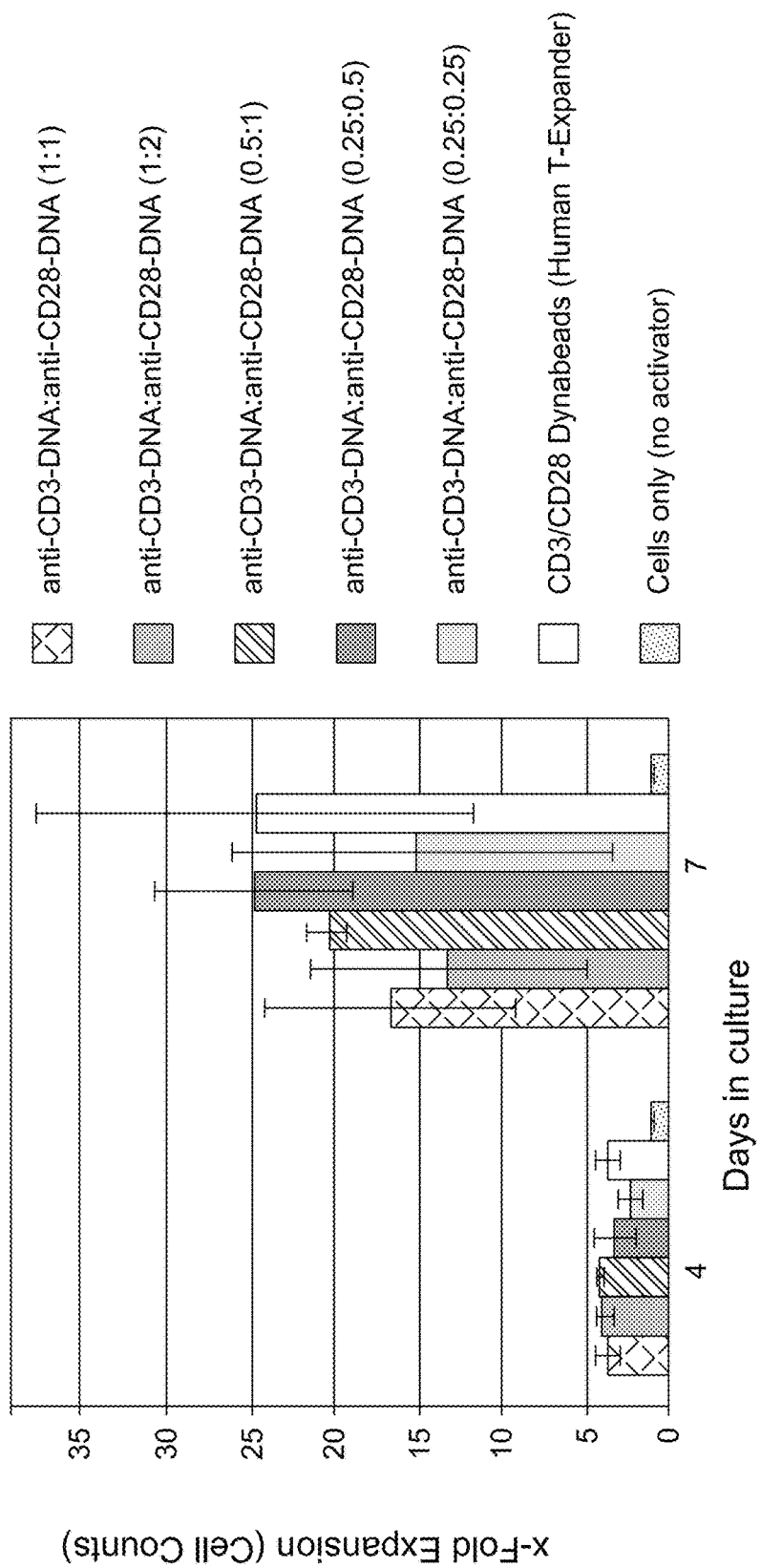
FIG. 6B is a graphical representation of cell expression of the same cultures as FIG. 6A after days 4 and 7 showing x-fold expansion (cell counts).

FIG. 6A shows that sufficient T cell activation (24-hour % CD25 expression) and FIG. 6B cell expansion (days 4 and 7) are achieved at a variety of input quantities of antibody and RCAact product. Not surprisingly, the lowest input quantities of both antibody conjugate (0.25 µg/mL input or ~170 pM) and the corresponding RCAact product (~17 nM) showed the lowest levels of 24-hour % CD25 expression (60%), although this level of activation still far exceeds the cells-only negative control (20%) and eventually leads to day 7-fold expansion that matches the benchmark Dynabead samples. It is noted that half the standard input quantity of Ab-DNA conjugate (0.5 µg/mL) and RCAact (33.5 nM) nonetheless achieves the same level of early activation (90%) as the Dynabead benchmark. The data for this example is derived from three separate experiments featuring five different human T cell donors and four different batches of Ab-DNA conjugates.

Example 8: The Effect of Pre-Incubating DBTA Antibody Conjugates with Cells Prior to the Addition of RCA Polymeric Product for T Cell Activation An experiment was conducted to assess the effect of adding the anti-CD3-DNA and anti-CD28-DNA antibody conjugates to T cell culture to generate a Ab-DNA/cell pre-incubated sample prior to a separate, second addition of RCA polymeric product 30 min later. For this experiment, all other protocol details and quantities outlined in Example 4 were followed.

Figure 7A:
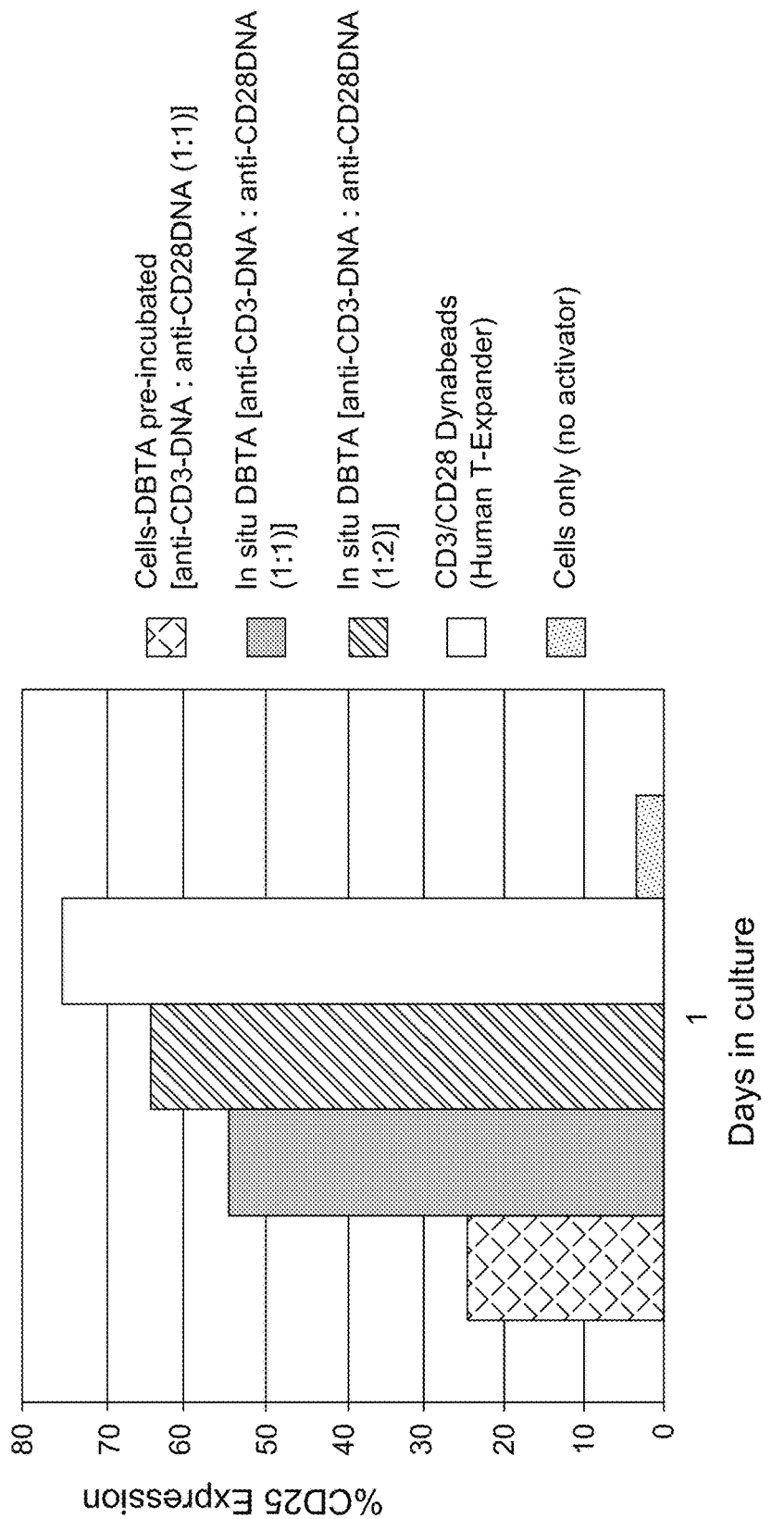
FIG. 7A is a graphical representation of greater than two-fold lower early activation (24-hour % CD25 expression) for sample where cells were pre-mixed with anti-CD3 and anti-CD28 DNA conjugates for 30 minutes prior to adding RCA compared to all three DTBA components added at once (one after another).
Figure 7B:
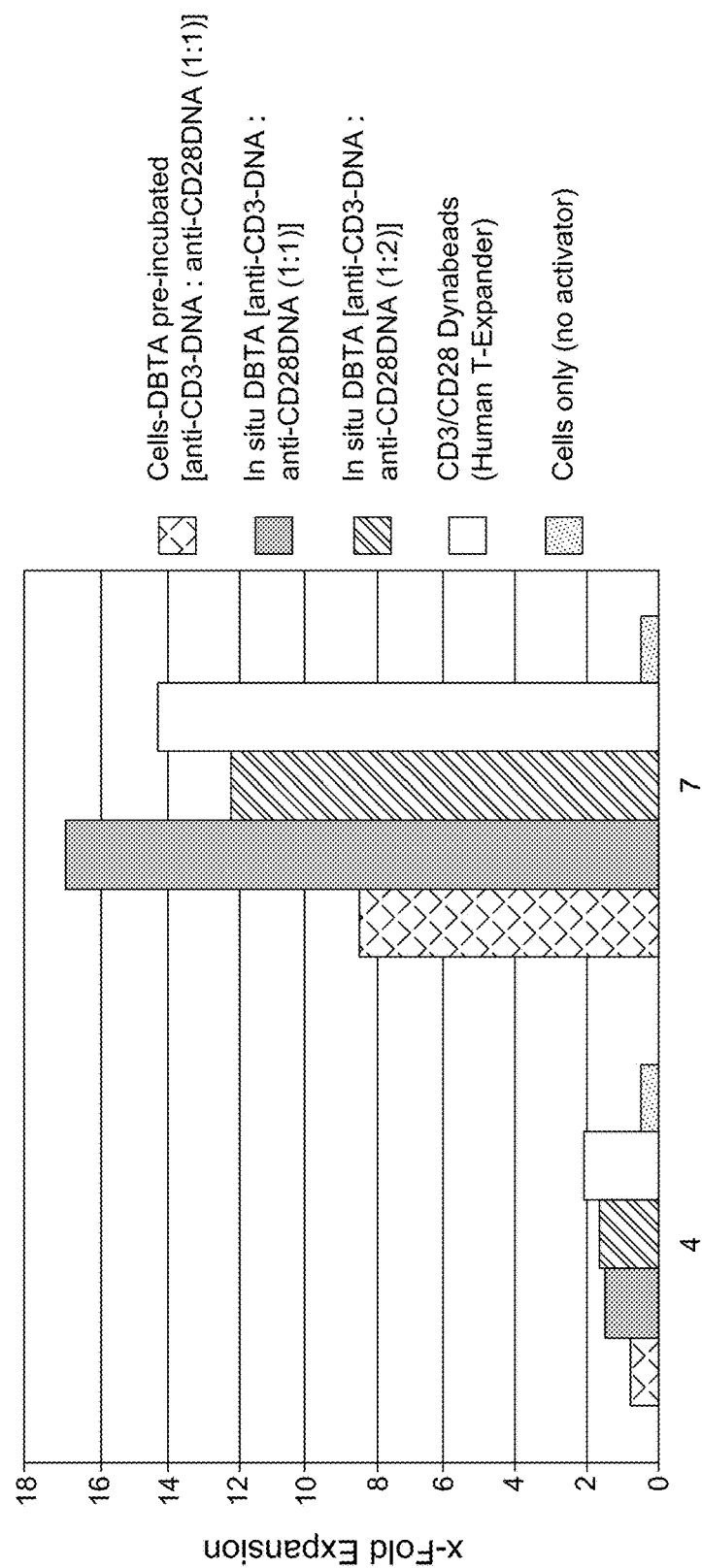
FIG. 7B is a graphical representation of the same cultures as FIG. 7A showing diminished day 7 cell expansion (x-fold expansion, cell counts).

FIG. 7A highlights a greater than two-fold lower early activation (24-hour % CD25 expression) and FIG. 7B shows diminished day 7 cell expansion for the Ab-DNA/cell pre-incubated sample (anti-CD3-DNA/anti-CD28-DNA DBTA (Ab-DNA/cells pre-incubated)) relative to both standard DBTA samples (featuring simultaneous addition of all components) (anti-CD3-DNA/anti-CD28-DNA DBTA in situ) and Dynabead controls. FIG. 7B also shows results of expansion after 4 days.

Example 9: The Effect of Different Input Ab-DNA Conjugate-to-RCA Product Ratios on T Cell Activation Efficiency A series of T cell activation experiments were conducted to assess the effect of different Ab-DNA conjugate-to-RCAact input ratios on T cell activation efficiency. In all cases, only anti-CD3-DNA (anti-CD3-o20b(+)act) conjugates were used. Each Ab conjugate sample, furthermore, featured the same standard concentration per well for activation (1 μg/mL input or ~6.7 μM), while a three log range of input RCAact product was investigated (6.7 nM, 67 nM, and 670 nM) to give starting Ab-DNA:RCA ratios of 1:1, 1:10, and 1:100, respectively. In addition, both CpG and non-CpG RCA template variants (see Example 1) were investigated. For these experiments, all other protocol details and quantities outlined in Example 4 were maintained.

Figure 8A:
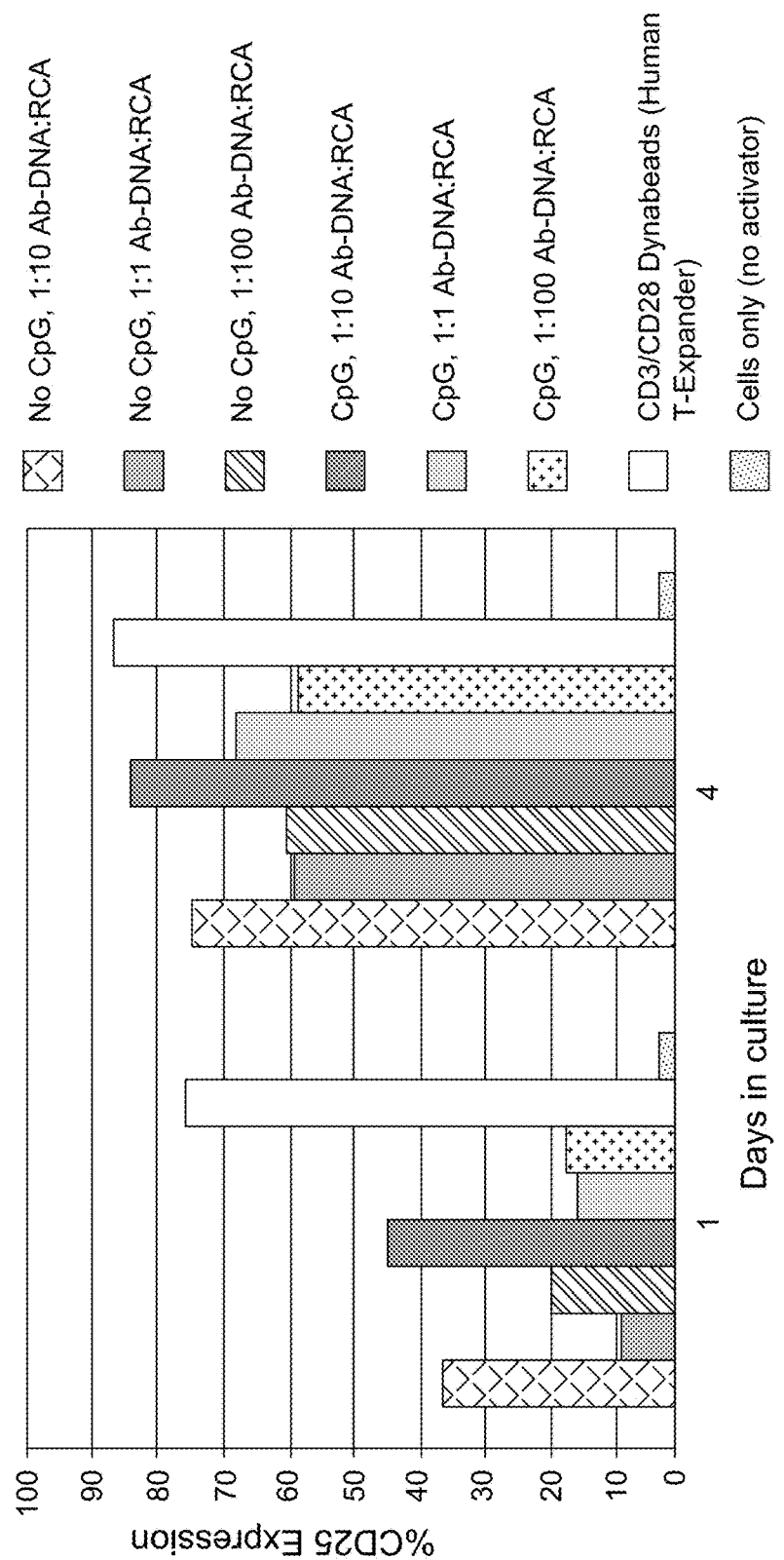
FIG. 8A is a graphical representation showing T cell activation (% CD25 expression) is achieved for both CpG and no CpG RCA at different ratios (1:1, 1:10 and 1:100) of the anti-CD3-DNA:RCAact.
Figure 8B:
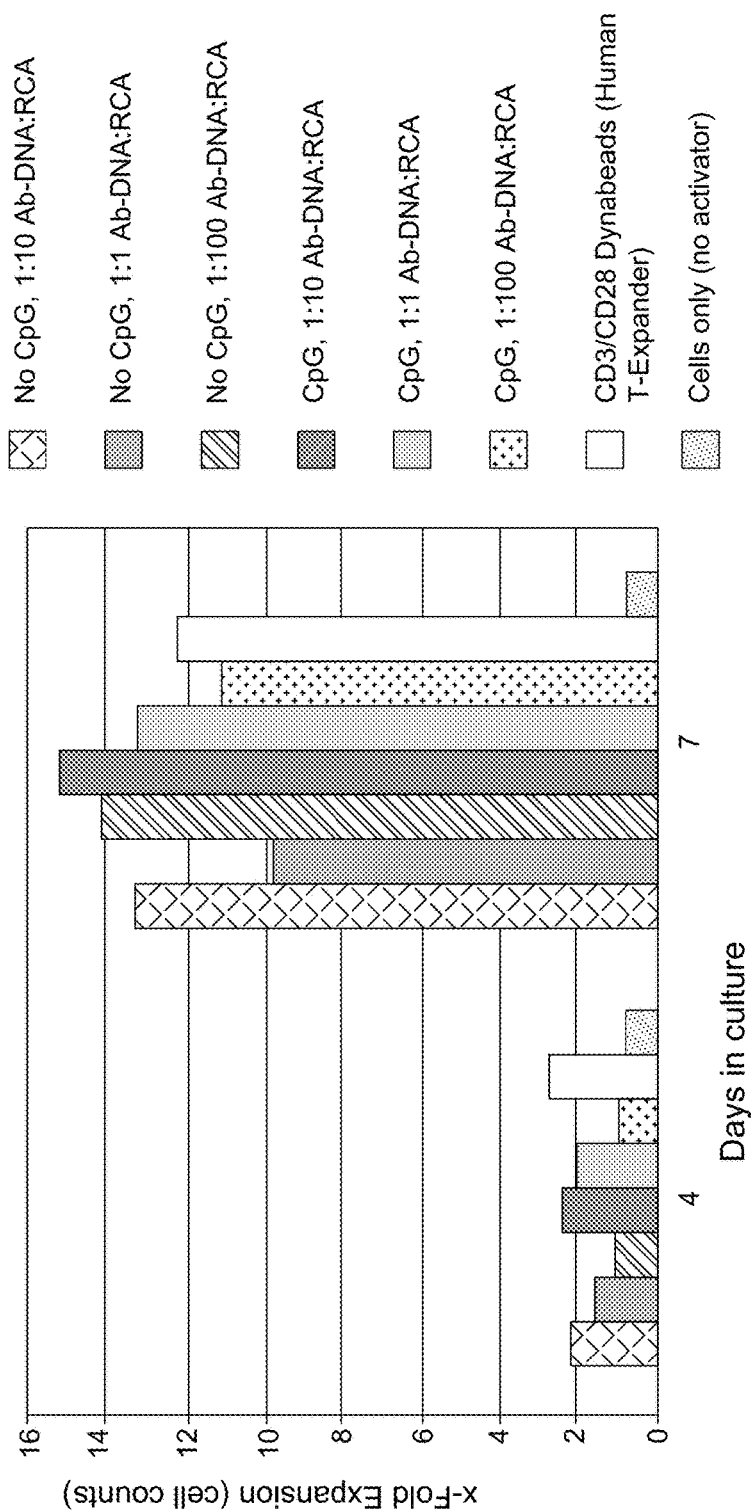
FIG. 8B is a graphical representation of the same cultures as FIG. 8A showing x-fold expansion (cell counts) after 4 and 7 days.

FIGS. 8A and 8B shows that optimal T cell activation (% CD25 expression) is achieved for both CpG and no CpG RCA at the anti-CD3-DNA:RCAact ratio of 1:10. Diminished activation efficiency is observed at both higher and lower ratios of Ab-DNA-to-RCA. All samples, however, demonstrate day 7 T cell expansion of about 10-fold or greater, matching or exceeding the Dynabead control sample. FIG. 8A is after 1 and 4 day culture showing % CD25, FIG. 8B is after 4 and 7 days showing x-fold expansion.

Example 10: Demonstration of Human T Cell Activation and Expansion Using an Alternative DBTA System with a Different Sequence and Oligo Length All previous examples (1-9) and associated FIGS. (1-8) for this disclosure successfully utilize a DBTA system featuring DNA sequences derived from human β-actin (Example 1). Successful human T cell activation and expansion may also be achieved with any number of alternative systems featuring different DNA sequences, base content, and oligo lengths. One alternative example features oligo and RCA products originally derived from the methicillin-resistant *Staphylococcus aureus* (MRSA) genome. The specific sequence information for each of these DBTA components is shown in Table 6 below:

TABLE 6

Sequence Information.

| Name | sense | length (b) | Sequence (5'→3') including modifications | SEQ ID NO | use/application |
|---|---|---|---|---|---|
| RCA primer (MRSA) | - | 20 | ATC AAT GAT GCA TAA CAT CT | 5 | primer for RCA reactions, sequence derived from MRSA genome |
| RCA template (MRSA) | + | 43 | /Phos/CAT CAT TGA TTT AGA CAC TGA AAA AGT TCG AGG AGA TGT TAT G | 6 | template for RCA reactions, sequence derived from MRSA genome |
| o25b(+)mrsa | + | 25 | /MalC6/CAT CAT TGA TTT AGA CAC TGA AAA A | 7 | conjugation to Ab via 5'-maleimide and binding to MRSA-derived RCA product |

Figure 9A:
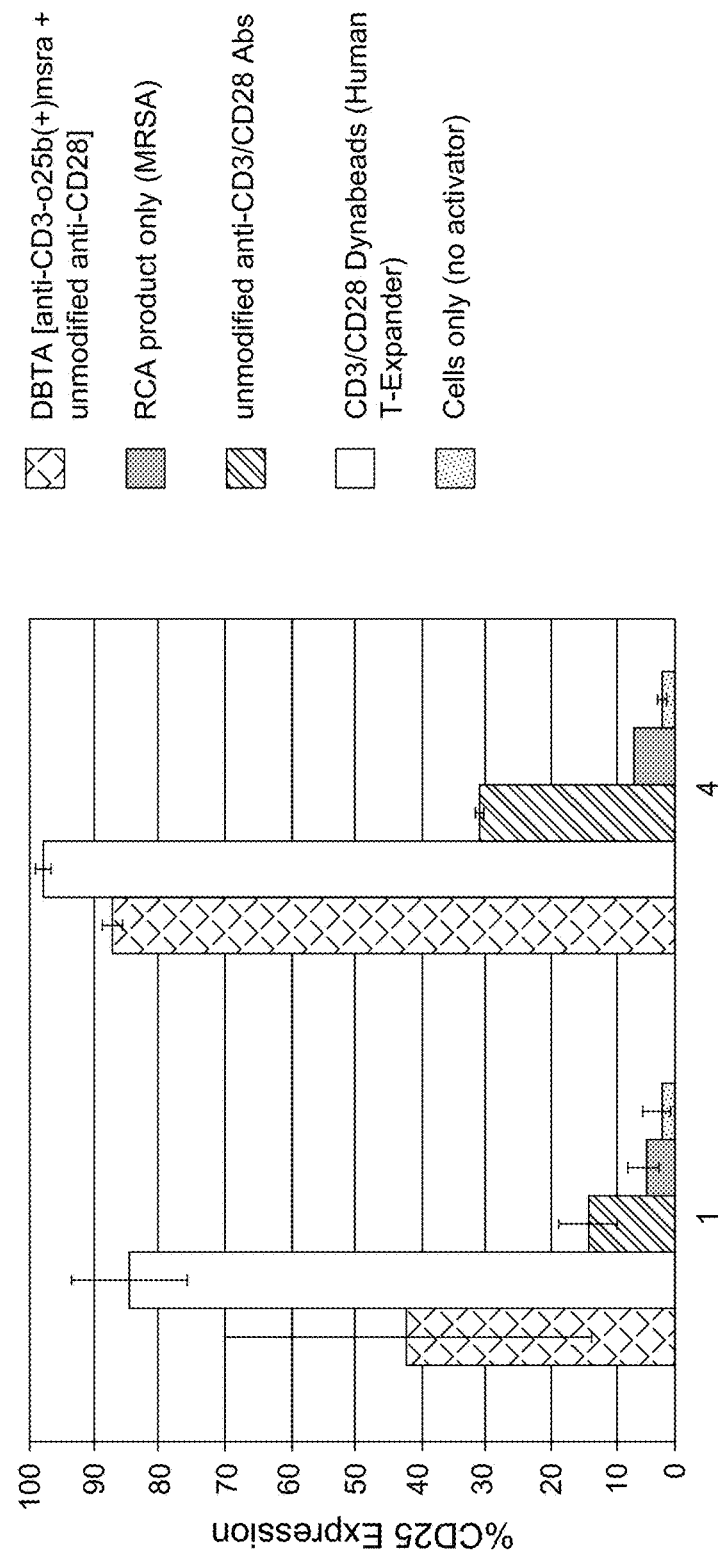
FIG. 9A is a graphical representation showing T cell activation with a different DNA sequence (a portion of MRSA (Methicillin-resistant *Staphylococcus aureus*) sequence) attached to the anti-CD3 antibody and its complementary RCA product.
Figure 9B:
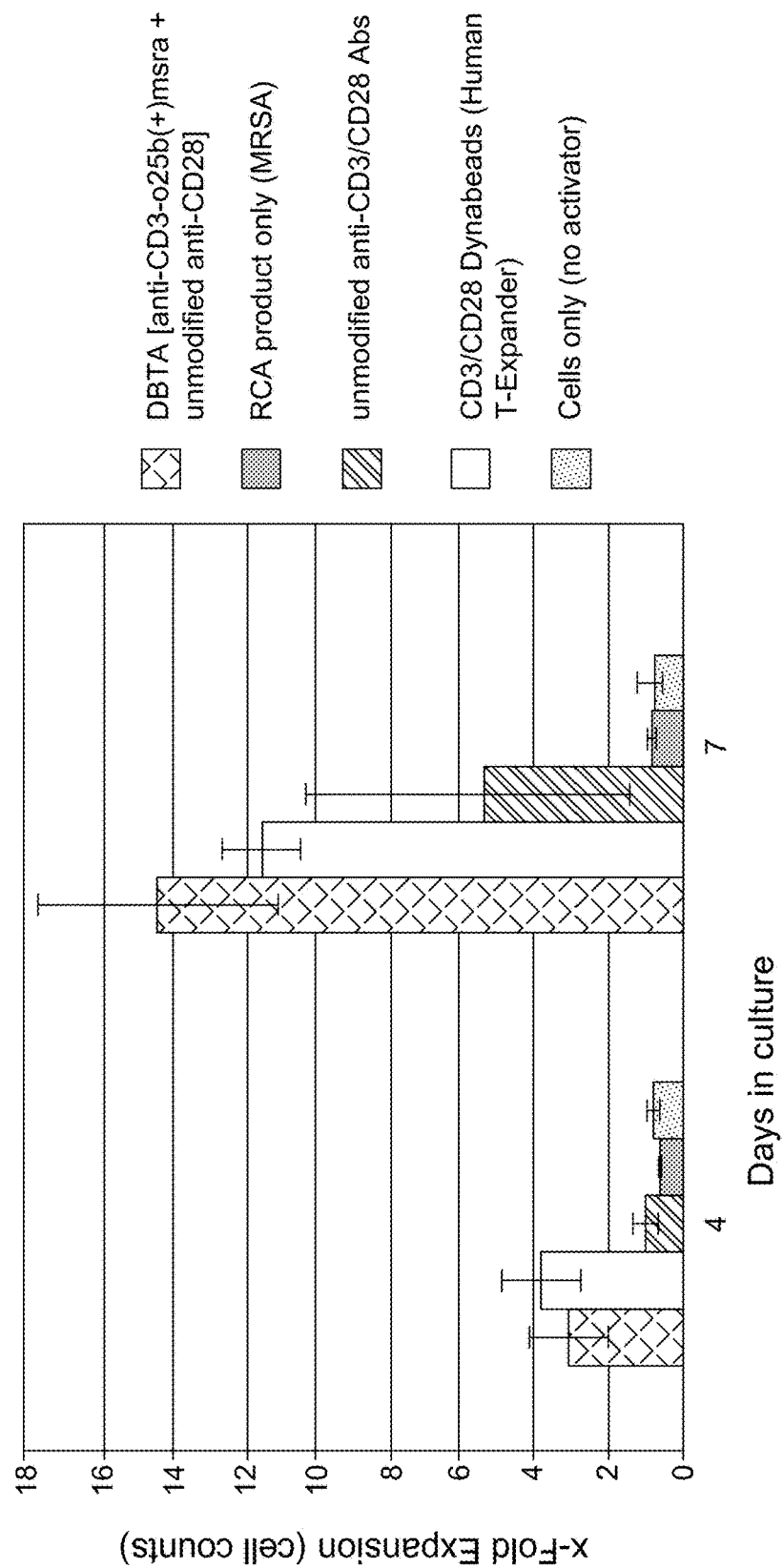

FIGS. 9 A and 9B shows clear, comparable performance of DBTA component (anti-CD3-DNA conjugate only with soluble anti-CD28 Ab) relative to the CD3/CD28 Dynabeads benchmark with respect to both early (days 1 and 4) % CD25 expression (FIG. 9A) as well as x-fold cell expansion after days 4 and 7 (FIG. 9B). These results are comparable to the β-actin derived DBTA system shown in the above examples. Also as with the β-actin DBTA, the specificity of the system is confirmed: control samples with unmodified antibodies, RCA product alone, and cells only show very low level of activation and expansion. It is noted that the exact same Ab conjugation, RCA production, and cell culturing protocols and molar quantities described above for β-actin DBTA were also utilized for the MRSA system.

Example 11: Demonstration of Human T Cell Activation and Expansion Using a DBTA System Featuring Cleaved RCA Polymeric Products A comparison of human T cell activation and expansion efficiency using different sized RCA products was conducted using the MRSA-based DBTA system (See Example 10 and Example 3 for general conditions used to generate full length RCA product). For these experiments, full length RCA products were subjected to sonication conditions yielding different relative size distributions. To produce sonicated RCA products, a Covaris M220 Focused Ultrasonicator™ (Covaris, Woburn, Mass.) was utilized according to the manufacturer's recommended input conditions to yield 1500 bp and 150 bp sized fragments starting from large genomic DNA fragments. Target input parameters include peak incident power, duty factor, cycles per burst, treatment time, and temperature. After sonication, analytical size exclusion chromatography was used according to Example 1 conditions to confirm the relative size distributions of products. While absolute size and molecular weight determinations are unknown for the RCA products by this method, we observed the expected general trend of increasing elution time for smaller fragments. The following elution times were thus observed: 10.1 min (corresponding to the void volume) for ~16 kb (theoretical maximum length) full length RCA product, 10.8 min for the 1.5 kb sonicated RCA product, 14.8 min for the 0.15 kb sonicated RCA product, 19.2 min for the starting 43b RCA template (control injection), 20.0 min for the unconjugated o25b(+)mrsa (control injection), and 23.7 min for residual small molecules including nucleotides.

Figure 10A:
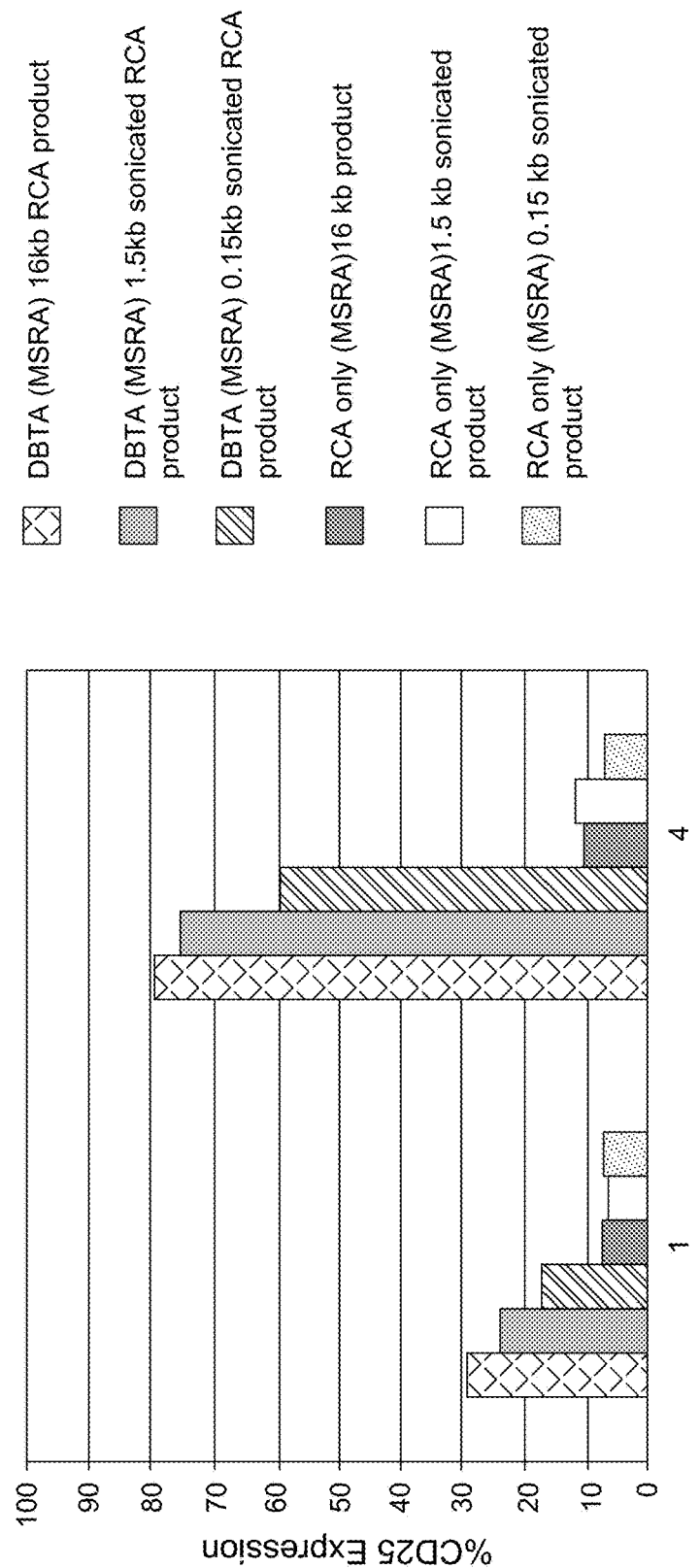
FIG. 10A is a graphical representation showing that the larger the RCA product, the higher the activation (% CD25 expression).
Figure 10B:
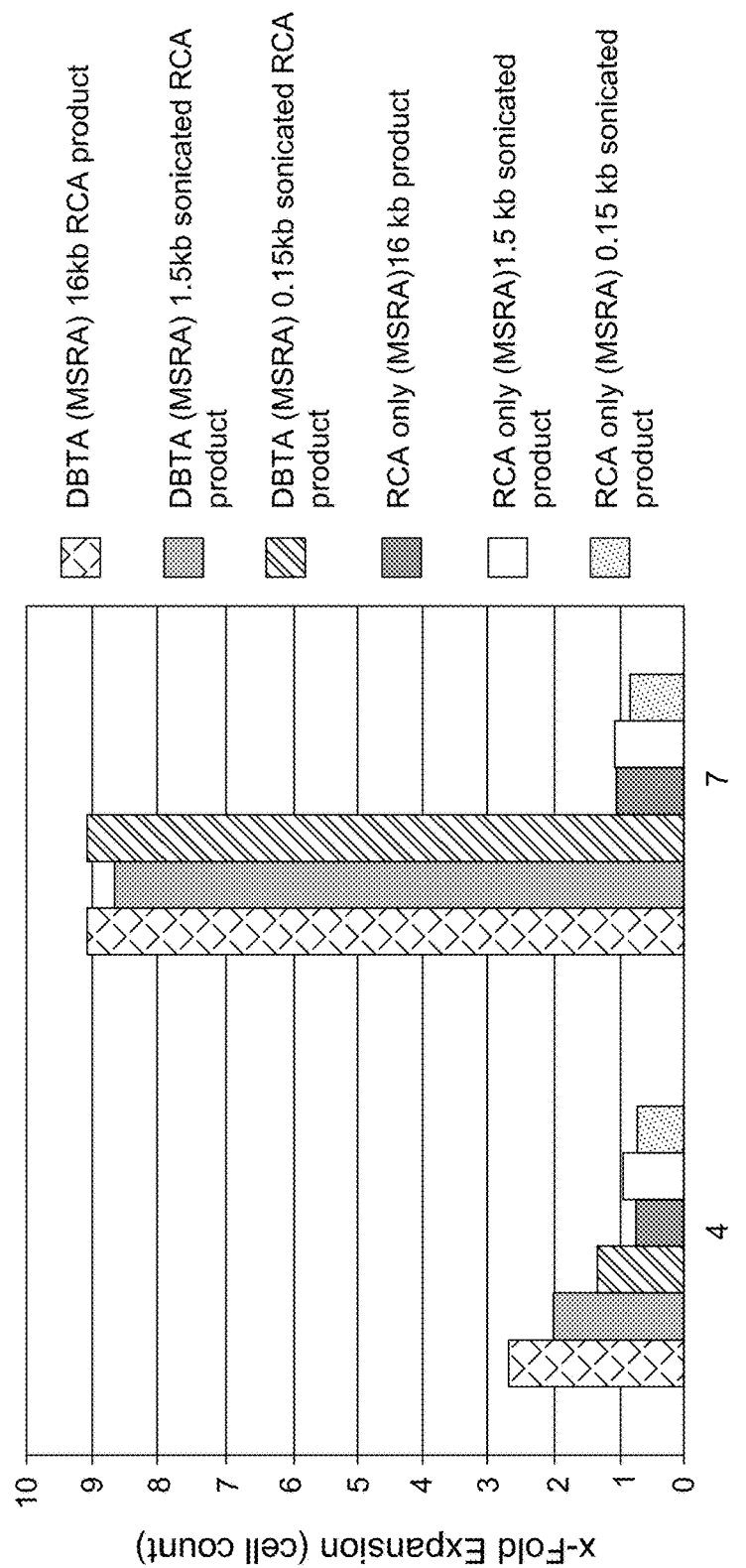
FIG. 10B is a graphical representation of the same cultures in FIG. 10A showing higher x-fold expansion (cell counts) with larger product in early expansion phase (day 4), however, by day 7 all the three RCA products of different sizes yield comparable levels of cell expansion.

FIGS. 10A and 10B shows that the larger the RCA product, the higher the activation (FIG. 10A % CD25 expression) and fold-expansion for the early days 1-4 of the experiment, while the trend becomes less pronounced later in the study. In particular, by day 7, all the three RCA products of different sizes yield comparable levels of cell expansion (FIG. 10B).

While only certain features of the invention have been illustrated and described herein, many modifications and changes will occur to those skilled in the art. It is, therefore, to be understood that the appended embodiments are intended to cover all such modifications and changes as fall within the scope of the invention.

The invention claimed is:

1. A method of activating T cells, the method comprising:
   a) providing a population of T cells;
   b) adding a plurality of first agents, wherein the first agent comprises a T-cell activator attached to a first binder moiety;
   c) adding a second agent comprising a plurality of capture oligomers, wherein at least a segment of at least one of the plurality of capture oligomers is capable of associating with the first binder moiety; and
   d) incubating the population of T cells after steps (b) and (c), whereby at least a portion of the population of T cells is activated.

2. The method of claim 1, wherein the second agent is a nucleic acid polymer comprising a plurality of capture oligonucleotide sequences.

3. The method of claim 2, wherein the second agent is a rolling circle amplification product comprising a plurality of capture oligonucleotide sequences.

4. The method of claim 2, wherein the first binder moiety is a nucleic acid sequence, wherein at least a segment of at least one of the plurality of capture oligonucleotide sequences is complementary to the nucleic acid sequence.

5. The method of claim 2, further comprising adding a nuclease.

6. The method of claim 1, wherein the T-cell activator is an anti-CD3 antibody or a fragment thereof.

7. The method of claim 1, further comprising adding a T-cell co-stimulator.

8. The method of claim 7 wherein the T-cell co-stimulator is an anti-CD28 antibody, an anti-CD2 antibody or fragments thereof.

9. The method of claim 7, wherein the T-cell co-stimulator is attached to a second binder moiety, wherein at least a segment of at least one of the plurality of capture oligomers is capable of associating with the second binder moiety.

10. The method of claim 9, wherein the second binder moiety is a nucleic acid sequence.

11. The method according to claim 7 where the T-cell activator is an anti-CD3 antibody attached to a nucleic acid sequence, the T-cell co-stimulator is an anti-CD28 antibody attached to a nucleic acid sequence, and the second agent is a rolling circle amplification product comprising of a plurality of complementary capture oligonucleotide sequences.

12. A method according to claim 1, further comprising a step of adding a vector comprising a foreign gene into the population of T cells.

13. A method according to claim 12, wherein the vector is added with the plurality of first agents.

14. A method according to claim 12, wherein the vector is added after at least a portion of the population of T cells is activated.

15. A method according to claim 12, wherein the vector is a lentivirus vector or a gamma-retrovirus vector.

16. The method of claim 1,
wherein the T-cell activator is an anti-CD3 antibody, the first binder moiety is a nucleic acid sequences, the second agent is a nucleic acid polymer and the plurality of capture oligomers is a plurality of capture oligonucleotide sequences, wherein at least a segment of at least one of the plurality of capture oligonucleotide sequences is complementary to the nucleic acid sequence attached to the anti-CD3 antibody.

17. The method of claim 16, further comprising adding an anti-CD28 antibody.

18. The method of claim 17, wherein the anti-CD28 antibody is attached to a nucleic acid sequence, wherein at least a segment of at least one of the plurality of capture oligonucleotide sequences is complementary to the nucleic acid sequence attached to the anti-CD28 antibody.

19. The method of claim 2, wherein the number of capture oligonucleotide sequences in the nucleic acid polymer is greater than 3.

20. The method of claim 2, wherein the plurality of capture oligonucleotide sequences have the same nucleotide sequence or have different nucleotide sequences.

21. A method of activating cells, the method comprising:
a) providing a population of cells selected from the group consisting of B cells, T cells and natural killer cells;
b) adding a plurality of first agents, wherein the first agent comprises a cell activator attached to a first binder moiety:
c) adding a second agent comprising a plurality of capture oligomers, wherein at least a segment of at least one of the plurality of capture oligomers is capable of associating with the first binder moiety; and
d) incubating the population of cells after steps (b) and (c), whereby at least a portion of the population of cells is activated.

22. The method of claim 21, wherein the second agent is a nucleic acid polymer comprising a plurality of capture oligonucleotide sequences.

23. The method of claim 22, wherein the second agent is a rolling circle amplification product comprising a plurality of capture oligonucleotide sequences.

24. The method of claim 22, wherein the first binder moiety is a nucleic acid sequence, wherein at least a segment of at least one of the plurality of capture oligonucleotide sequences is complementary to the nucleic acid sequence.

25. The method of claim 24, wherein the cell activator is attached to the nucleic acid sequence via a covalent attachment.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgactattaa gacttcctgt                                                    20

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate

<400> SEQUENCE: 2
ttaatagtca ttccaaatat gagatgcgtt gttacaggaa gtc                          43

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate

<400> SEQUENCE: 3
ttaatagtca ttccaacata tgagatggtt gttacaggaa gtc                          43

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Maleimide functional group and C6 spacer
```

```
<400> SEQUENCE: 4
acaggaagtc ttaatagtca                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atcaatgatg cataacatct                                              20

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate

<400> SEQUENCE: 6
catcattgat ttagacactg aaaaagttcg aggagatgtt atg                    43

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Maleimide functional group and C6 spacer

<400> SEQUENCE: 7
catcattgat ttagacactg aaaaa                                        25
```